United States Patent
Harris et al.

(10) Patent No.: US 11,160,550 B2
(45) Date of Patent: Nov. 2, 2021

(54) SURGICAL STAPLING END EFFECTOR COMPONENT WITH ARTICULATION AND ASYMMETRIC DEFORMABLE TIP

(71) Applicant: ETHICON LLC, Guaynabo, PR (US)

(72) Inventors: Jason L. Harris, Lebanon, OH (US); Gregory J. Bakos, Mason, OH (US); Chester O. Baxter, III, Loveland, OH (US); Frederick E. Shelton, IV, Hillsboro, OH (US)

(73) Assignee: Cilag GmbH International, Zug (CH)

(*) Notice: Subject to any disclaimer, the term of this patent is extended or adjusted under 35 U.S.C. 154(b) by 158 days.

(21) Appl. No.: 16/035,825

(22) Filed: Jul. 16, 2018

(65) Prior Publication Data

US 2020/0015813 A1    Jan. 16, 2020

(51) Int. Cl.
| | | |
|---|---|---|
| A61B 17/072 | (2006.01) | |
| A61B 17/28 | (2006.01) | |
| A61B 17/29 | (2006.01) | |
| A61B 17/064 | (2006.01) | |

(52) U.S. Cl.
CPC .......... *A61B 17/072* (2013.01); *A61B 17/282* (2013.01); *A61B 17/2909* (2013.01);
(Continued)

(58) Field of Classification Search
CPC . A61B 17/072; A61B 17/282; A61B 17/2909; A61B 17/2017; A61B 17/0645;
(Continued)

(56) References Cited

U.S. PATENT DOCUMENTS

| | | |
|---|---|---|
| 4,805,823 A | 2/1989 | Rothfuss |
| 5,014,899 A | 5/1991 | Presty et al. |

(Continued)

FOREIGN PATENT DOCUMENTS

| | | |
|---|---|---|
| EP | 2772202 | 9/2014 |
| WO | WO 2004/096057 | 11/2004 |

(Continued)

OTHER PUBLICATIONS

European Search Report dated Aug. 7, 2018 for Application No. 18157228.0, 8 pages.
(Continued)

*Primary Examiner* — Dariush Seif
(74) *Attorney, Agent, or Firm* — Frost Brown Todd LLC

(57) ABSTRACT

An instrument includes a body, a shaft, and an end effector. The shaft extends from the body and defines a shaft axis extending longitudinally along the shaft. The end effector is operable to compress, staple, and cut tissue. The end effector includes first and second opposing jaws, a staple cartridge, and a placement tip. At least one of the jaws is movable relative to the other jaw between an open position and a closed position. The staple cartridge is coupled with the second jaw. The placement tip extends from a distal end of one of the jaws and includes proximal and distal portions. The distal portion includes an asymmetric profile along the longitudinal axis of the shaft. The distal portion includes a tip axis defined by a tip of the distal portion. The shaft axis and the tip axis define an angle that is selectively adjustable.

18 Claims, 18 Drawing Sheets

(52) U.S. Cl.
CPC ............... *A61B 2017/0645* (2013.01); *A61B 2017/07221* (2013.01); *A61B 2017/07257* (2013.01); *A61B 2017/07271* (2013.01); *A61B 2017/07285* (2013.01); *A61B 2017/2913* (2013.01); *A61B 2017/2926* (2013.01); *A61B 2017/2946* (2013.01)

(58) Field of Classification Search
CPC ........ A61B 17/07221; A61B 17/07257; A61B 17/07271; A61B 17/07285; A61B 17/2913; A61B 17/2926; A61B 17/2946
USPC .............. 227/175.1–182.1; 606/75, 219, 220
See application file for complete search history.

(56) References Cited

U.S. PATENT DOCUMENTS

| | | | |
|---|---|---|---|
| 5,275,608 A * | 1/1994 | Forman | A61B 17/29 606/170 |
| 5,397,324 A * | 3/1995 | Carroll | A61B 17/07207 128/898 |
| 5,415,334 A | 5/1995 | Williamson et al. | |
| 5,465,895 A | 11/1995 | Knodel et al. | |
| 5,501,654 A * | 3/1996 | Failla | A61B 17/0218 600/204 |
| 5,597,107 A | 1/1997 | Knodel et al. | |
| 5,601,578 A * | 2/1997 | Murphy | A61B 17/0469 606/148 |
| 5,618,294 A * | 4/1997 | Aust | A61B 17/29 606/170 |
| 5,632,432 A | 5/1997 | Schulze et al. | |
| 5,649,957 A * | 7/1997 | Levin | A61B 17/29 606/205 |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,704,210 B1 * | 3/2004 | Myers | A61B 17/07207 349/150 |
| 6,755,815 B2 * | 6/2004 | Schultz | A61B 17/00234 606/1 |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,780,054 B2 * | 8/2010 | Wales | A61B 17/00234 227/175.1 |
| 7,806,891 B2 | 10/2010 | Nowlin et al. | |
| 8,066,166 B2 | 11/2011 | Demmy et al. | |
| 8,136,711 B2 | 3/2012 | Beardsley et al. | |
| 8,210,411 B2 | 7/2012 | Yates et al. | |
| 8,348,123 B2 | 1/2013 | Scirica et al. | |
| 8,353,092 B2 * | 1/2013 | Nguyen | A61B 17/06 29/447 |
| 8,403,195 B2 | 3/2013 | Beardsley et al. | |
| 8,403,196 B2 * | 3/2013 | Beardsley | A61B 17/068 227/175.1 |
| 8,408,439 B2 | 4/2013 | Huang et al. | |
| 8,453,914 B2 | 6/2013 | Laurent et al. | |
| 8,479,969 B2 | 7/2013 | Shelton | |
| 8,496,153 B2 | 7/2013 | Demmy et al. | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,628,544 B2 | 1/2014 | Farascioni | |
| 8,690,039 B2 | 4/2014 | Beardsley et al. | |
| 8,714,429 B2 | 5/2014 | Demmy | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 8,844,790 B2 | 9/2014 | Demmy et al. | |
| 9,016,546 B2 | 4/2015 | Demmy et al. | |
| 9,039,736 B2 | 5/2015 | Scirica et al. | |
| 9,186,142 B2 | 11/2015 | Fanelli et al. | |
| 9,301,759 B2 | 4/2016 | Spivey et al. | |
| 9,433,416 B2 | 9/2016 | Beardsley et al. | |
| 9,517,065 B2 * | 12/2016 | Simms | A61B 17/07207 |
| 9,522,004 B2 | 12/2016 | Demmy | |
| 9,597,078 B2 | 3/2017 | Scirica et al. | |
| 9,622,746 B2 * | 4/2017 | Simms | A61B 17/07207 |
| 9,713,470 B2 | 7/2017 | Scirica et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,913,642 B2 | 3/2018 | Leimbach et al. | |
| 9,936,952 B2 * | 4/2018 | Demmy | A61B 17/07207 |
| 9,936,968 B2 | 4/2018 | Demmy et al. | |
| 9,943,311 B2 | 4/2018 | Scirica et al. | |
| 10,080,564 B2 | 9/2018 | Beardsley et al. | |
| 10,154,852 B2 * | 12/2018 | Conlon | A61B 17/320068 |
| 10,166,023 B2 | 1/2019 | Vendely et al. | |
| 2001/0034535 A1 * | 10/2001 | Schultz | A61B 17/00234 606/190 |
| 2004/0243151 A1 * | 12/2004 | Demmy | A61B 17/105 606/139 |
| 2005/0119669 A1 * | 6/2005 | Demmy | A61B 17/07207 606/139 |
| 2005/0216055 A1 | 9/2005 | Scirica et al. | |
| 2008/0169330 A1 * | 7/2008 | Shelton | A61B 17/205 227/180.1 |
| 2008/0237297 A1 * | 10/2008 | Demmy | A61B 17/07207 227/176.1 |
| 2013/0112729 A1 * | 5/2013 | Beardsley | A61B 17/07207 227/175.1 |
| 2013/0131651 A1 * | 5/2013 | Strobl | A61B 17/29 606/1 |
| 2013/0334280 A1 * | 12/2013 | Krehel | A61B 17/07207 227/176.1 |
| 2014/0012247 A1 * | 1/2014 | Bakos | H02J 50/10 606/33 |
| 2014/0166723 A1 | 6/2014 | Beardsley et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239043 A1 | 8/2014 | Simms et al. | |
| 2014/0239044 A1 | 8/2014 | Hoffman | |
| 2014/0263555 A1 * | 9/2014 | Hufnagel | A61B 17/068 227/176.1 |
| 2014/0288555 A1 * | 9/2014 | Okada | A61B 18/1492 606/46 |
| 2015/0173752 A1 | 6/2015 | Demmy et al. | |
| 2015/0209030 A1 * | 7/2015 | Kostrzewski | A61B 17/07207 227/177.1 |
| 2015/0209037 A1 * | 7/2015 | Kostrzewski | A61B 17/0682 227/178.1 |
| 2015/0272575 A1 | 10/2015 | Leimbach et al. | |
| 2015/0282809 A1 | 10/2015 | Shelton, IV et al. | |
| 2016/0135871 A1 * | 5/2016 | Kulkarni | A61B 18/1445 606/52 |
| 2016/0143659 A1 | 5/2016 | Glutz et al. | |
| 2016/0278774 A1 | 9/2016 | Shelton, IV et al. | |
| 2017/0055981 A1 | 3/2017 | Vendely et al. | |
| 2017/0086823 A1 | 3/2017 | Leimbach et al. | |
| 2017/0105725 A1 * | 4/2017 | Scheib | A61B 17/3209 |

(56) References Cited

U.S. PATENT DOCUMENTS

| | | | |
|---|---|---|---|
| 2017/0105787 A1* | 4/2017 | Witt | A61B 18/1445 |
| 2017/0224343 A1* | 8/2017 | Baxter, III | A61B 17/32 |
| 2017/0303954 A1* | 10/2017 | Ishii | A61B 17/32 |
| 2018/0199942 A1* | 7/2018 | Scirica | A61B 17/07207 |
| 2018/0221050 A1* | 8/2018 | Kostrzewski | A61B 17/3421 |
| 2018/0235609 A1 | 8/2018 | Harris et al. | |
| 2018/0235610 A1 | 8/2018 | Harris et al. | |
| 2018/0235611 A1 | 8/2018 | Harris et al. | |
| 2018/0235619 A1 | 8/2018 | Harris et al. | |
| 2018/0325514 A1 | 11/2018 | Harris et al. | |
| 2018/0325515 A1 | 11/2018 | Harris et al. | |
| 2018/0325516 A1 | 11/2018 | Harris et al. | |
| 2019/0000538 A1* | 1/2019 | Widenhouse | A61B 18/1442 |
| 2019/0076143 A1* | 3/2019 | Smith | A61B 34/30 |

FOREIGN PATENT DOCUMENTS

| | | |
|---|---|---|
| WO | WO 2013/151888 A1 | 10/2013 |
| WO | WO 2017/083129 | 5/2017 |

OTHER PUBLICATIONS

International Search Report and Written Opinion dated Apr. 19, 2018 for International Application No. PCT/US2018/017751, 17 pages.

U.S. Appl. No. 60/466,378, filed Apr. 29, 2003.
U.S. Appl. No. 60/843,254, filed Sep. 8, 2006.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,803, filed Jul. 16, 2018.
U.S. Appl. No. 16/035,821, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,865, filed Jul. 16, 2018.
U.S. Appl. No. 16/035,872, filed Jul. 16, 2018.
Design U.S. Appl. No. 29/594,332, filed Feb. 17, 2017.
Design U.S. Appl. No. 29/594,335, filed Feb. 17, 2017.
Design U.S. Appl. No. 29/594,340, filed Feb. 17, 2017.
European Search Report and Written Opinion dated Nov. 15, 2019 for Application No. EP 19186259.8, 9 pgs.
International Search Report and Written Opinion dated Nov. 20, 2019 for Application No. PCT/IB2019/055978, 15 pgs.

* cited by examiner

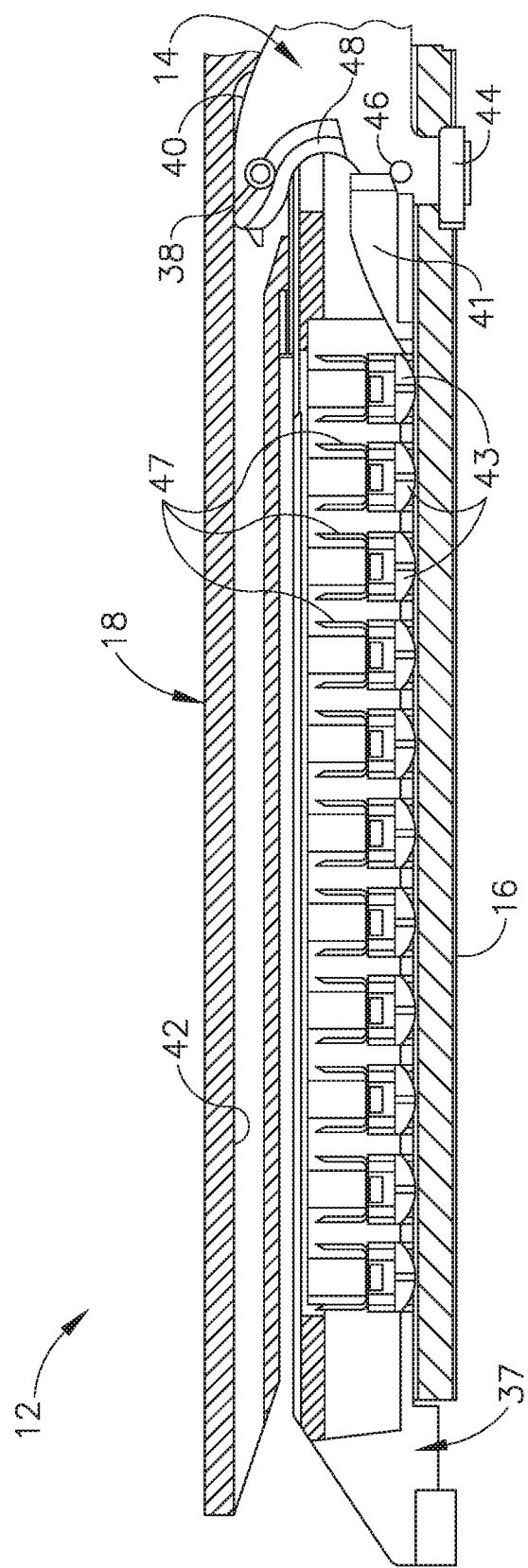

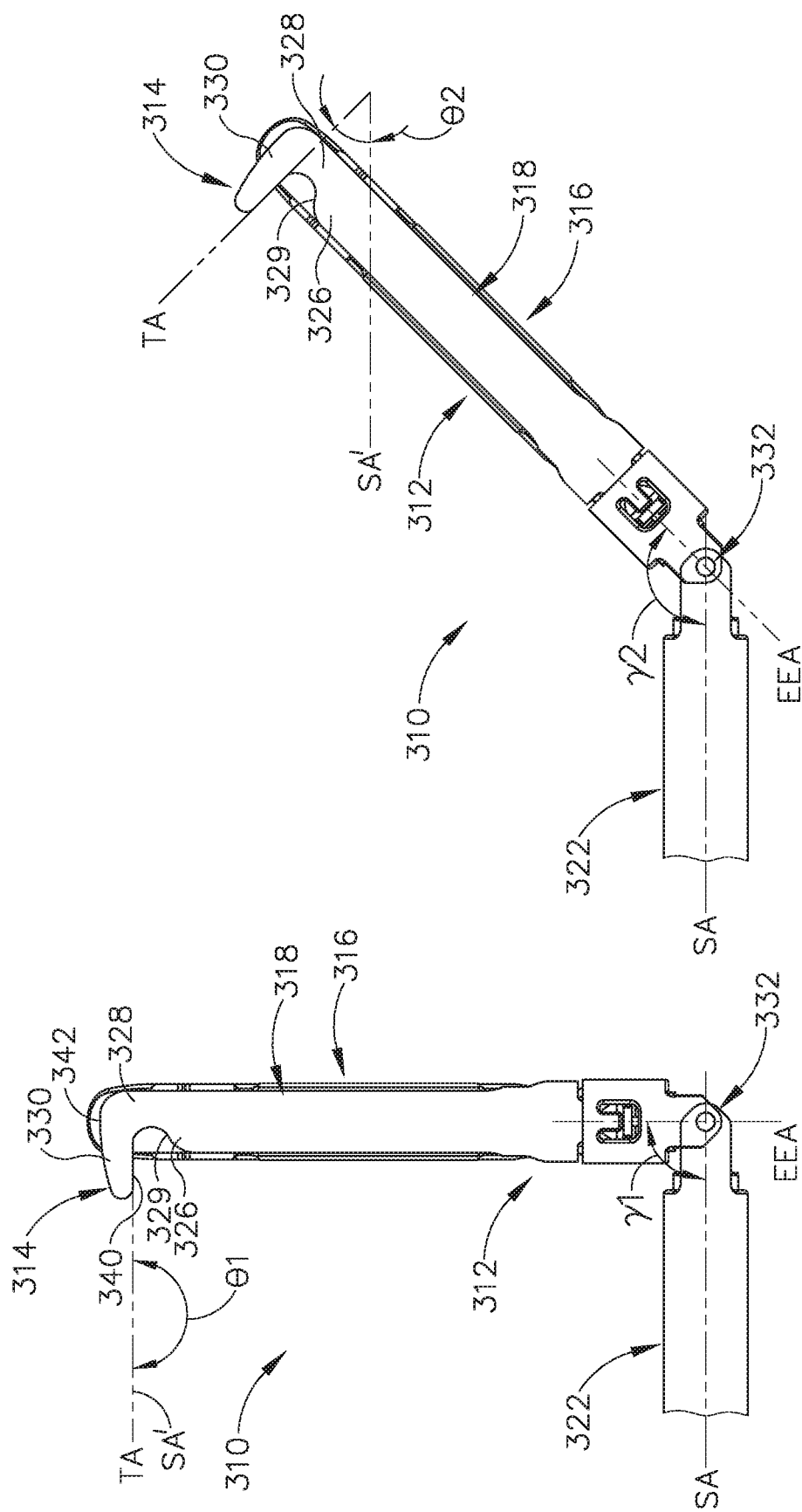

SURGICAL STAPLING END EFFECTOR COMPONENT WITH ARTICULATION AND ASYMMETRIC DEFORMABLE TIP

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts a side cross-sectional view of the end effector of FIG. 3, taken along line 4-4 of FIG. 3, with the firing beam in a proximal position;

FIG. 12A depicts an enlarged top view of the end effector of FIG. 11 in a first angled position;

FIG. 12B depicts an enlarged top view of the end effector of FIG. 11 in a second angled position;

Figure 1:
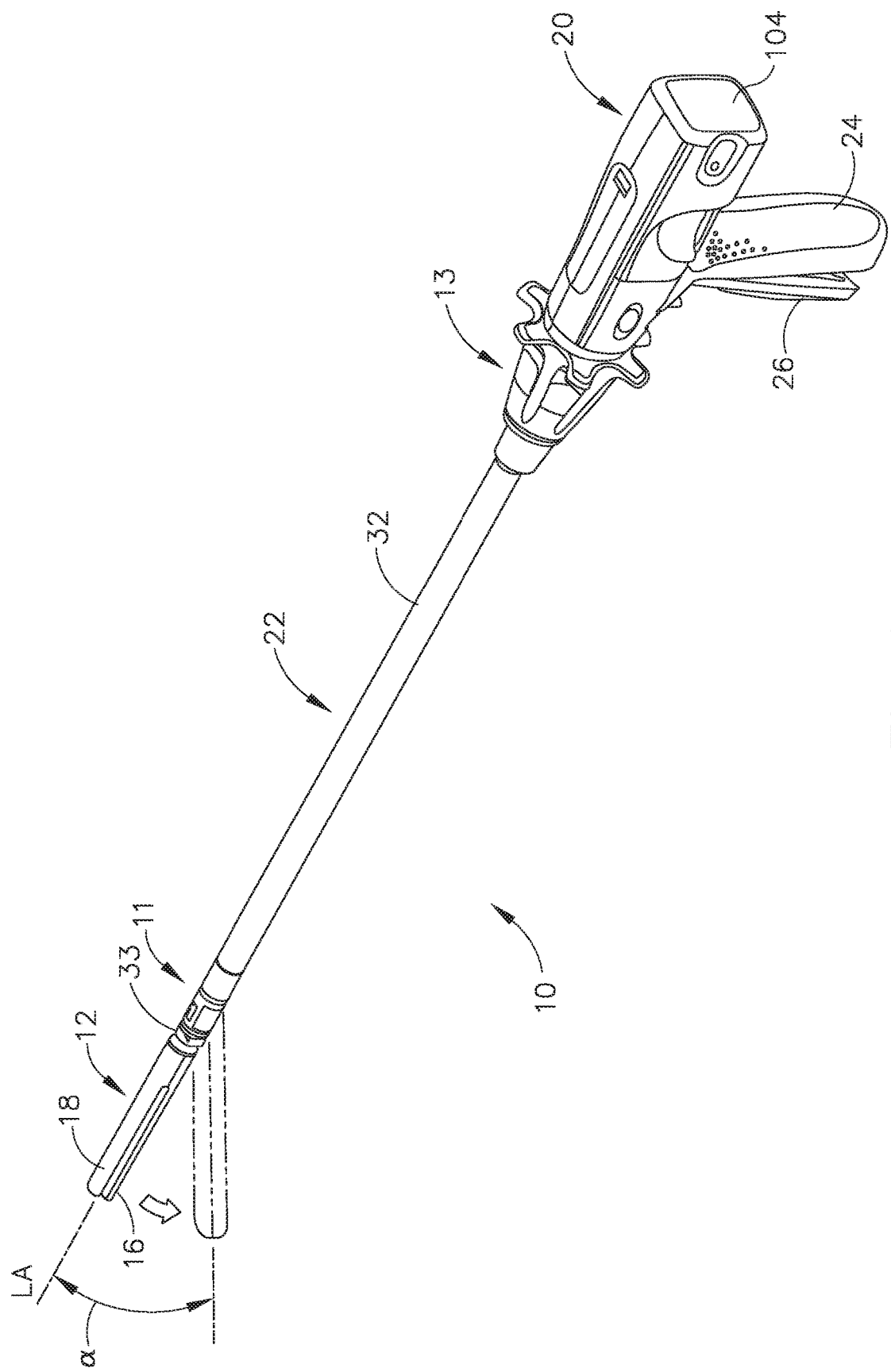
FIG. 1 depicts a perspective view of a first exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Surgical Instrument Having a First Exemplary End Effector

FIGS. 1-7 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (α). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
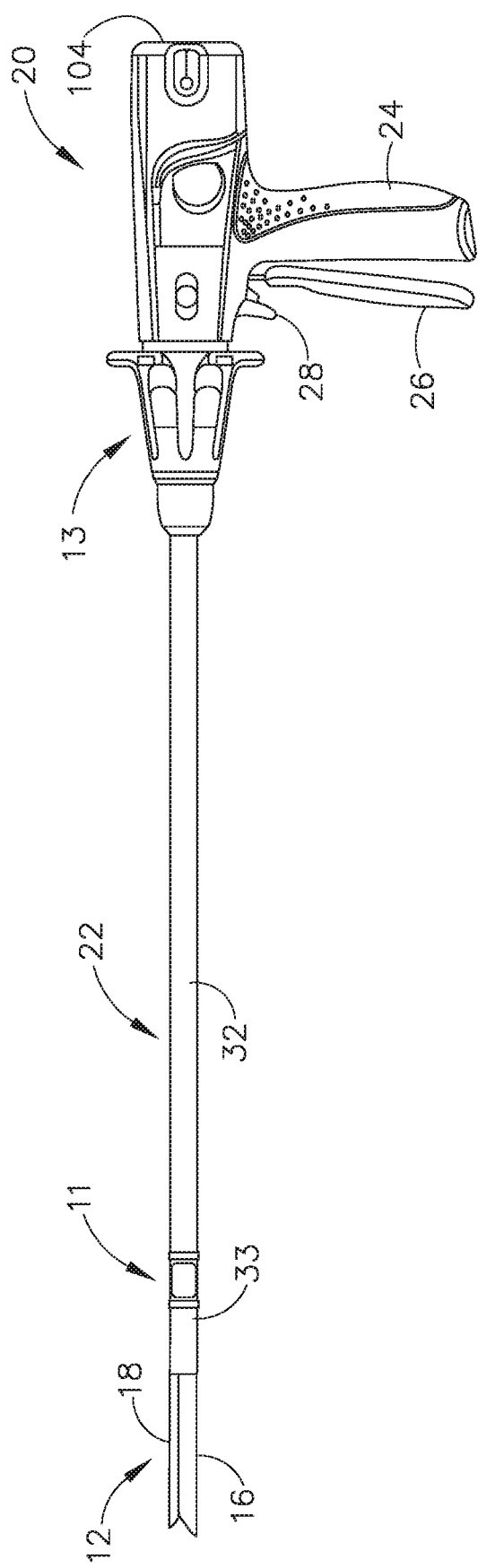
FIG. 2 depicts a side view of the instrument of FIG. 1 with a first exemplary end effector.

Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
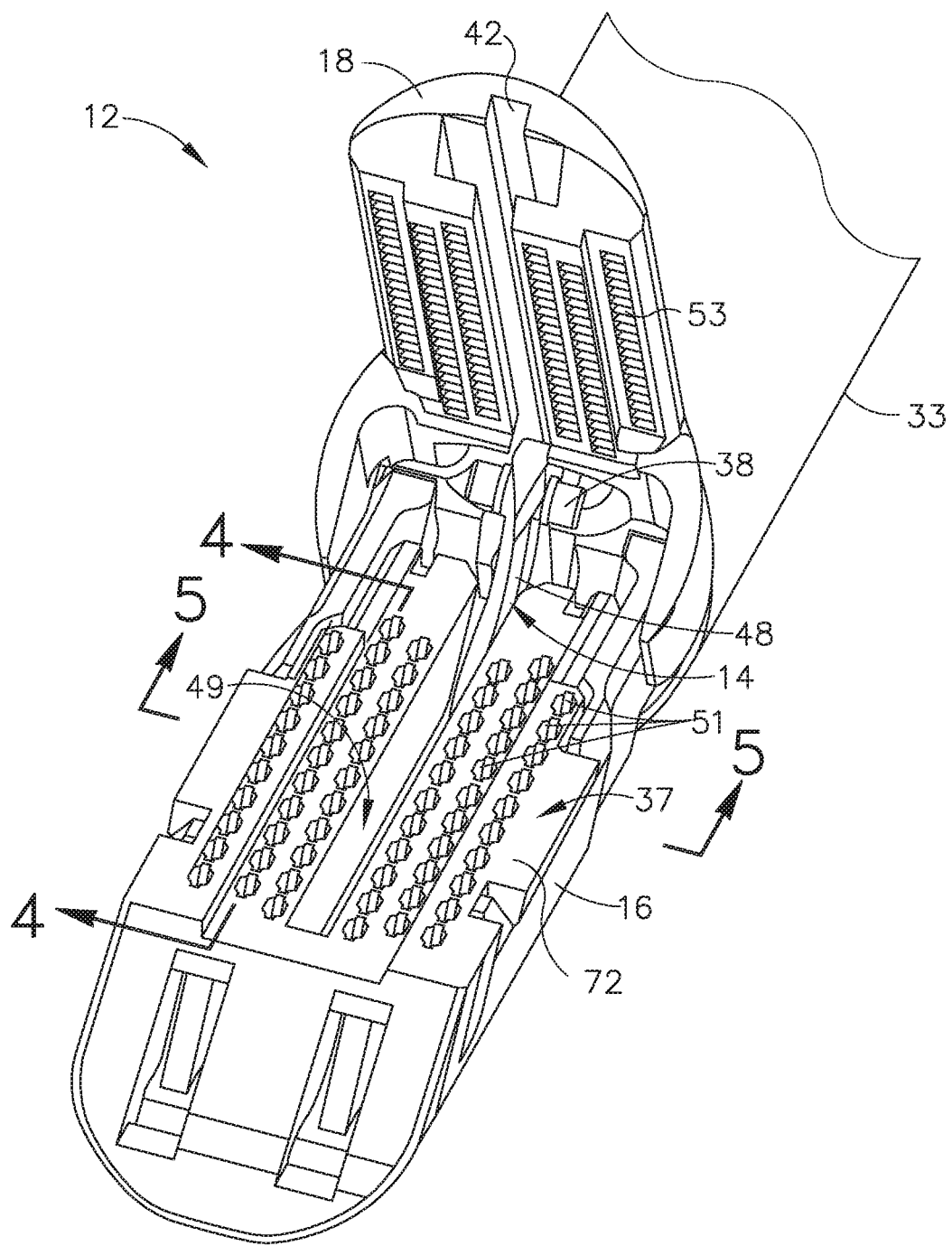
FIG. 3 depicts a perspective view of the end effector of the instrument of FIG. 1 in an open configuration.
Figure 4B:
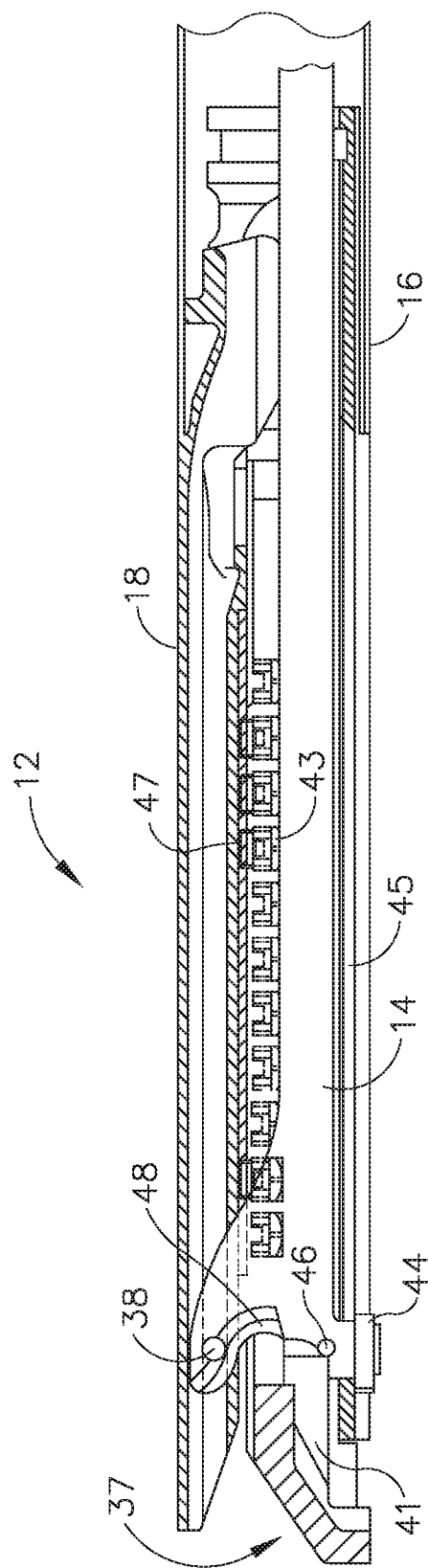
FIG. 4B depicts a side cross-sectional view of the end effector of FIG. 3, taken along line 4-4 of FIG. 3, with the firing beam in a distal position.
Figure 5:
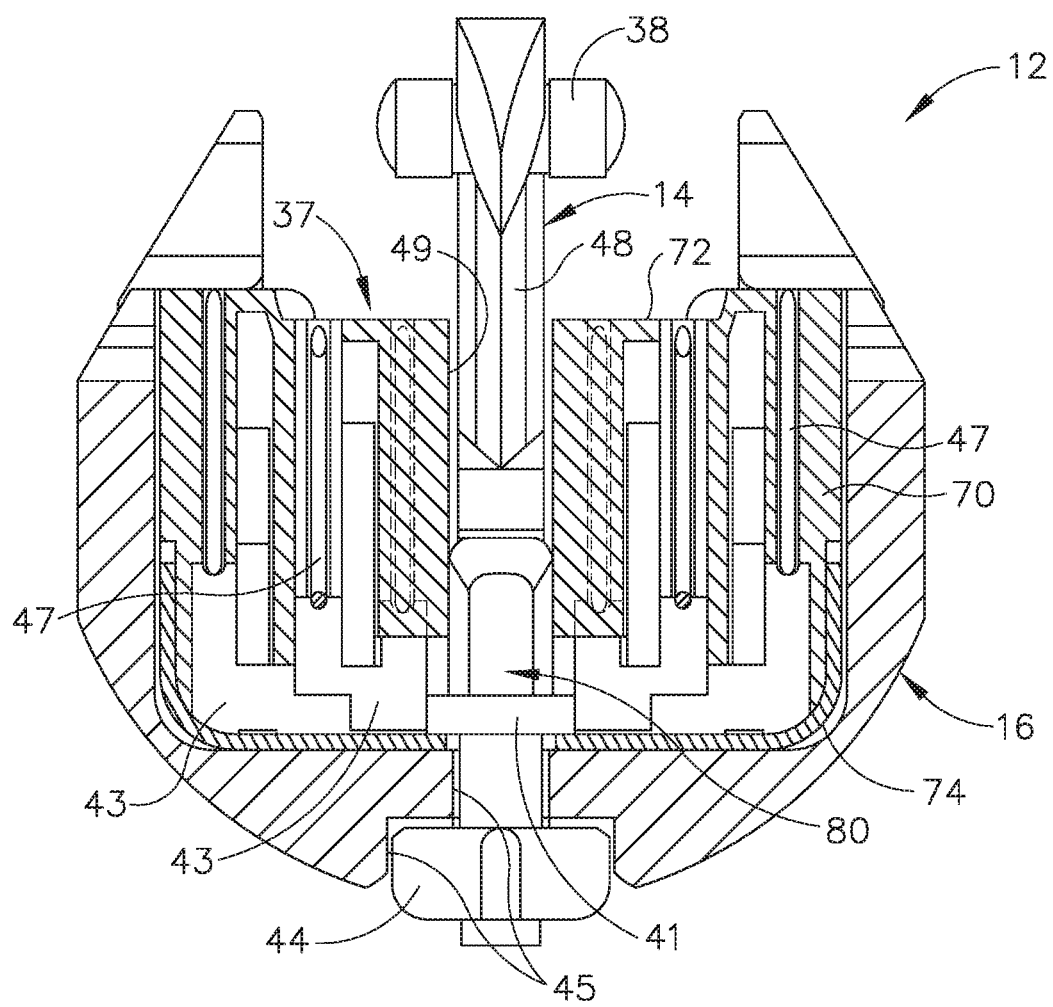
FIG. 5 depicts an end cross-sectional view of the end effector of FIG. 3, taken along line 5-5 of FIG. 3.
Figure 6:
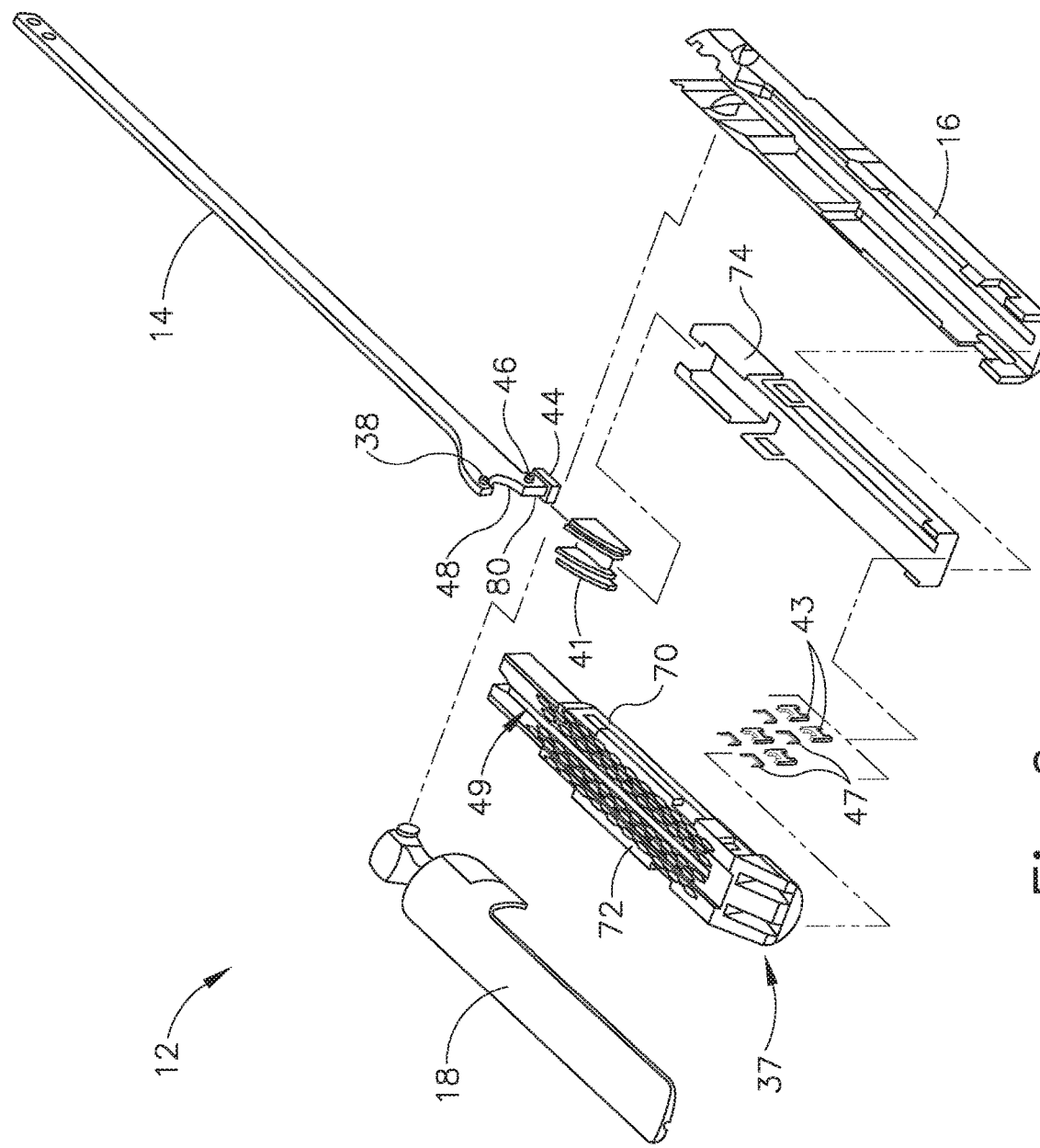
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples

(47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5.

Figure 7:
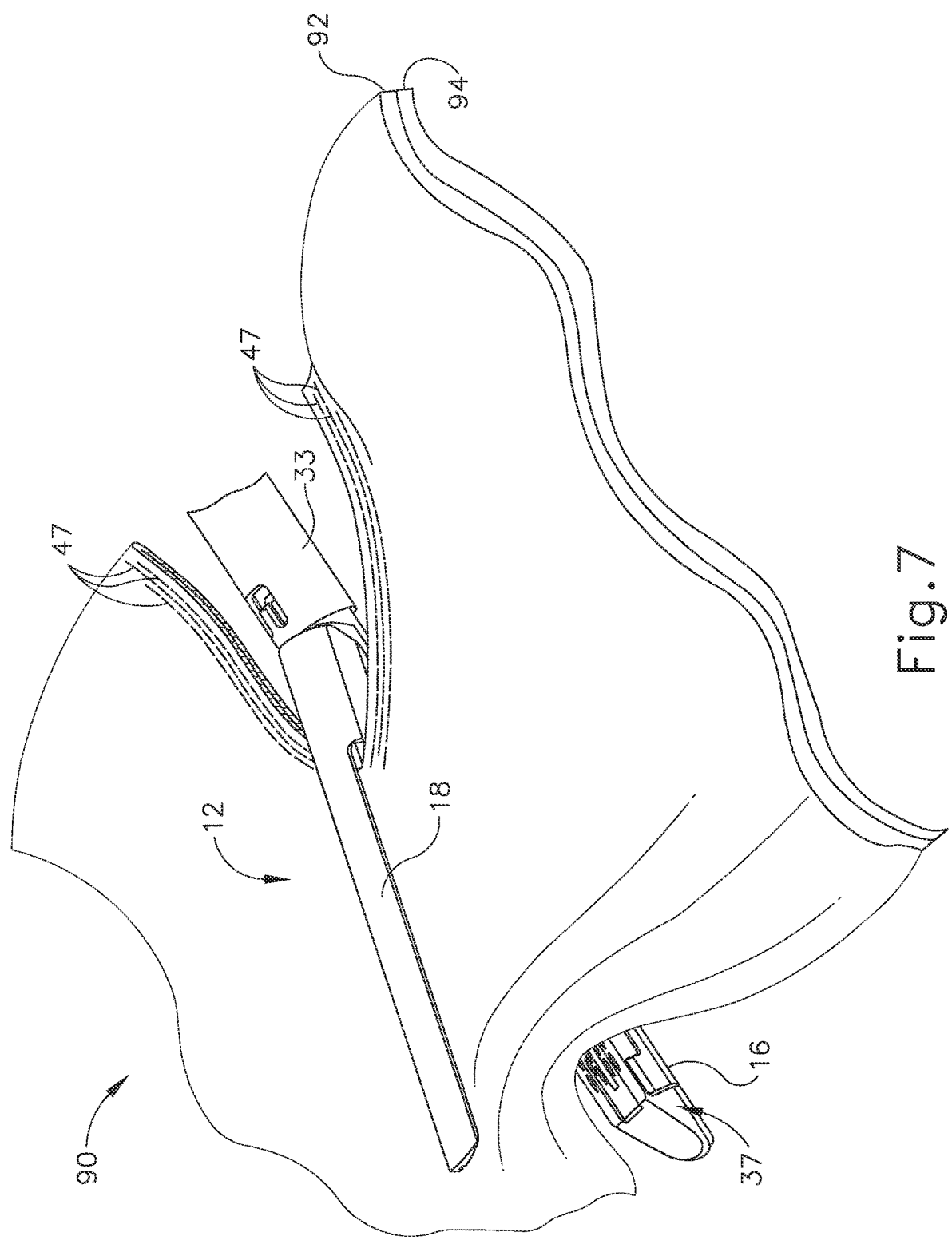
FIG. 7 depicts a perspective view of the end effector of FIG. 3, positioned at tissue and having been actuated once in the tissue.

FIG. 7 shows end effector (12) having been actuated through a single stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). End effector (12) is withdrawn from the patient after the first stroke is complete, spent staple cartridge (37) is replaced with a new staple cartridge, and end effector (12) is then again inserted to reach the stapling site for further cutting and stapling. This process may be repeated until the desired number of cuts and staples (47) have been provided.

Some versions of instrument (10) provide motorized control of firing beam (14). Such motorized control may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein; and/or U.S. Pat. No. 8,210,411, entitled "Motor-Driven Surgical Instrument," issued Jul. 3, 2012, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition, or in the alternative, the pivot axis may slide along the slot/channel first, with anvil (18) then pivoting about the pivot axis after the pivot axis has slid a certain distance along the slot/channel. Such sliding/translating pivotal movement is encompassed within terms such as "pivot," "pivots," "pivotal," "pivotable," "pivoting," and the like.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. First Exemplary Surgical Instrument Having a Second Exemplary End Effector

As end effector (12) is inserted into a surgical site, the user may rotate shaft (22) and end effector (12) of instrument (10) during the procedure. In some instances, lower jaw (16) of end effector (12) is visible rather than anvil (18); while in other instances anvil (18) is visible rather than lower jaw (16). It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely encompass the vessel to be cut, such that the vessel may be fully cut and stapled in one single actuation. It may be desirable to enable the operator to more easily visually confirm proper position of anvil (18) and lower jaw (16) in relation to a vessel to fully clamp the vessel. One potential way of enhancing visualization of the surgical site may include improving visualization of the area adjacent to the distal tip of lower jaw (16) and anvil (18). It may also be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
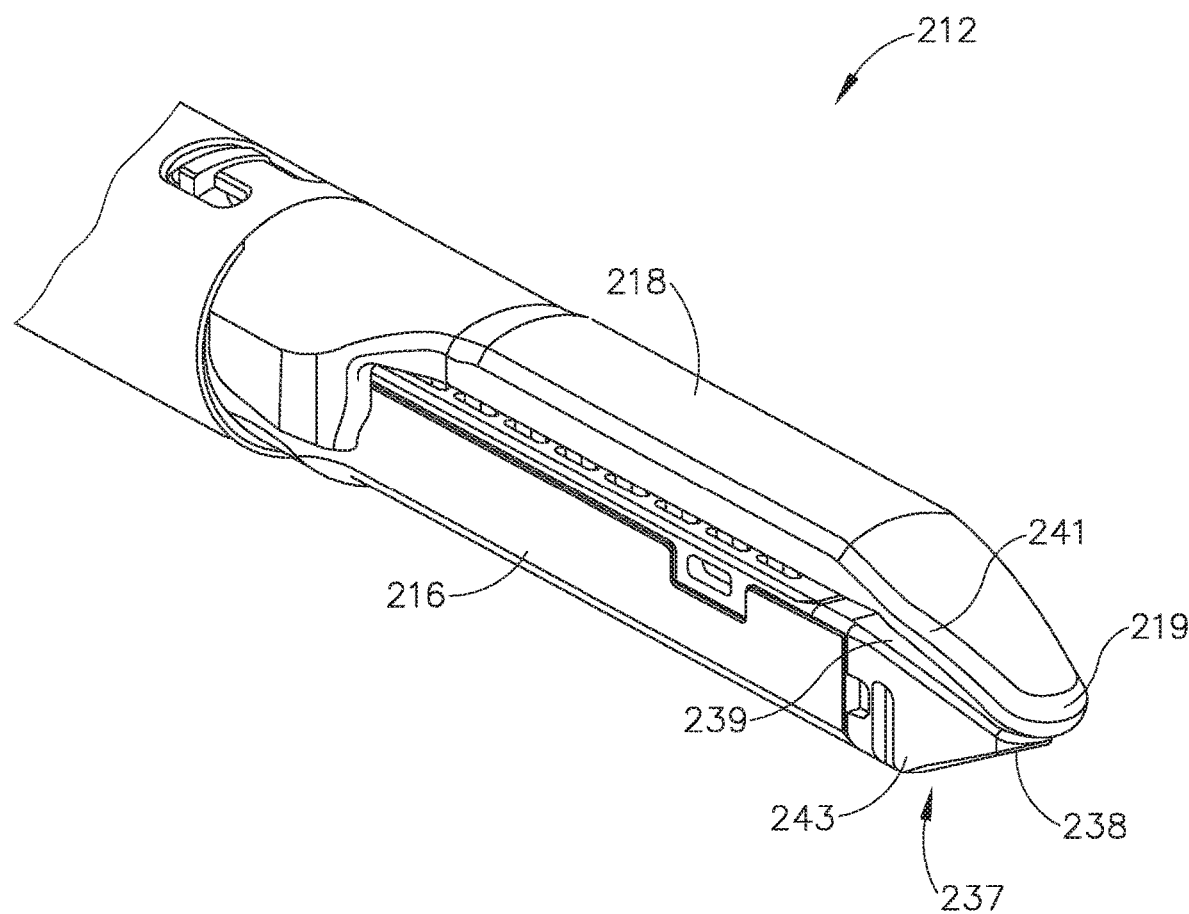
FIG. 8 depicts a perspective view of a second exemplary end effector that includes an angled cartridge and an angled anvil with a tip.

FIG. 8 depicts a second exemplary end effector (212) comprising an anvil (218) and a lower jaw (216). End effector (212) may be used in place of end effector (12) of instrument (10). End effector (212) may be integrally formed with instrument (10) or, in the alternative, may be interchangeable with end effector (12) of instrument (10). Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
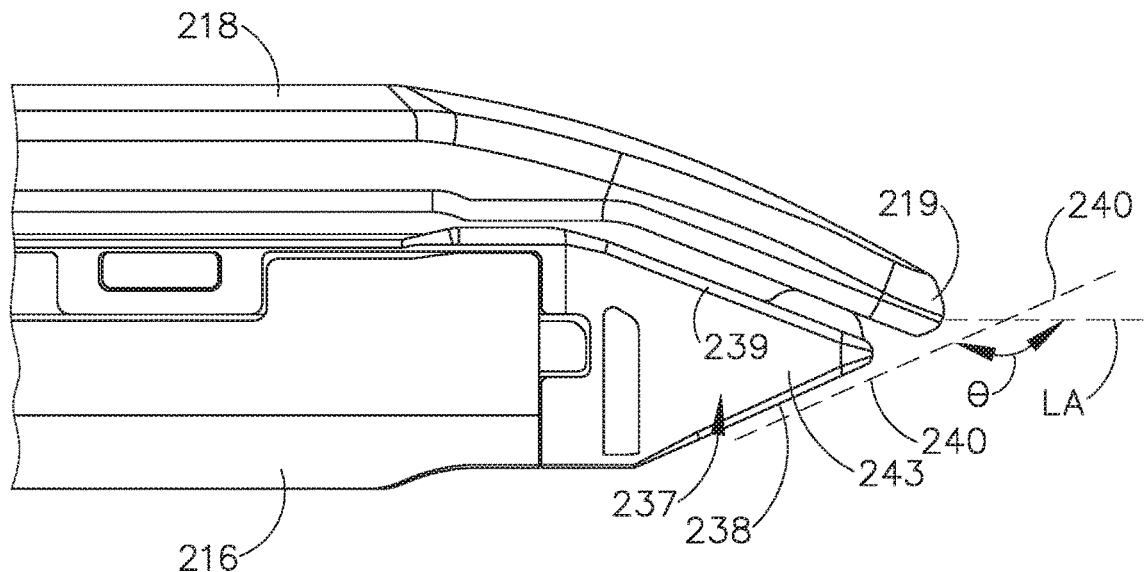
FIG. 9 depicts an enlarged side view of the end effector of FIG. 8.
Figure 10:
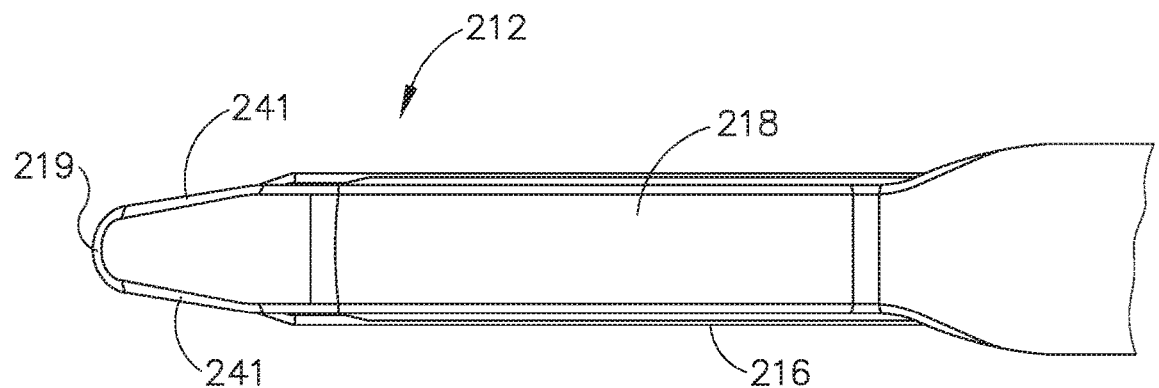
FIG. 10 depicts an enlarged top view of the end effector of FIG. 8.

Anvil (218) as shown in FIGS. 8-10 has an elongated shape where the distal portion of anvil (218) angles toward cartridge (237) such that the distal most tip (219) of anvil (218) extends distally longitudinally further than cartridge (237). Alternatively, distal most tip (219) may extend to a distance longitudinally equal to cartridge (237) or proximal relative to the distal most point on cartridge (237). As seen best in FIG. 10, anvil (218) includes sides (241) that taper laterally as they approach the distal most tip (219) of anvil (218). The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site.

Cartridge (237) is operable to hold staples like staples (47) shown in FIG. 4A for driving into tissue. As shown in FIG. 9, the distal end of cartridge (237) has a triangular profile defined by an upper tapered surface (239) and a lower tapered surface (238). The distal end of cartridge (237) also comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). Sight line (240) intersects longitudinal axis (LA), which extends longitudinally through end effector (212), to form a viewing angle (θ).

The planar shape of lower tapered surface (238) facilitate visualization of the distal most tip (219) of anvil (218). Viewing angle (θ) may establish the relative visibility that a user has of distal most tip (219), such that the user can see in front of distal most tip (219) along any line of sight that passes through the intersection of sight line (240) and longitudinal axis (LA) within viewing angle (θ). As viewing angle (θ) increases, the user would have greater visibility of the area immediately in front of distal most tip (219) from proximal vantage points; whereas as viewing angle (θ) decreases, the user has less visibility of the area in front of distal most tip (219) from proximal vantage points. In some versions, viewing angle (θ) defines an angle greater than 90 degrees. Additionally, in some versions, viewing angle (θ) defines an angle greater than 135 degrees. In the illustrated version, the user generally looks along sight line (240) or along some other line of sight within viewing angle (θ), such that the user has visibility along sight line as well as any area within viewing angle (θ). The underside of distal most tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). In some instances, end effector (212) may be rotated before, during, or after clamping tissue (90). As a result, the tapered shape of anvil (218) may also provide more accessible viewing of distal most tip (219) or substantially adjacent distal most tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). Lower tapered surface (238) and the tapered shape of anvil (218) may provide a lead-in, guiding the rest of end effector (212) into the trocar. Visibility and maneuverability may thus be enhanced by the tapered design for both sides (241) of anvil (218) and each side (243) of cartridge (237).

In addition to the foregoing, end effector (212) and versions of instrument (10) incorporating end effector (212) may be configured and operable in accordance the teachings of any one or more of the patent references cited herein. Further modifications that may be incorporated into end effector (212) will be described in greater detail below.

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then be removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages, such as enhanced visualization, maneuverability, and/or tissue-gathering effects. However, in versions where all the structures of end effector (212) are rigid, the bent configuration of distal most tip (219) of anvil (218) may not lend itself well to marching operations, as distal most tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all the tissue that is to be cut and stapled is gathered proximal to distal most tip (219).

In view of the foregoing, it may be desirable to provide a variation of end effectors (12, 212) that provides the marching capabilities of end effector (12), the improved visibility, maneuverability, and tissue-gathering effects associated with end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. Providing a deformable tip can provide an additional level of maneuverability benefits in terms of navigating through tissue to a surgical site. In this manner, the deformable tip may deflect or deform to promote smooth and atraumatic movement of the end effector through tissue, particularly during marching operations.

III. Second Exemplary Surgical Instrument Including End Effector with Placement Tip FIGS. 11, 12A-12E, and 13A-13D show a second exemplary surgical instrument (310), configured as a surgical stapler, that comprises a third exemplary end effector (312) and a first exemplary placement tip (314). End effector (312) includes an upper jaw and a lower jaw (316), with the upper jaw including an anvil (318). Instrument (310) additionally includes a body, shown as a handle portion (320), and a shaft (322) that extends from handle portion (320). As shown in FIGS. 11 and 12A-12E, shaft (322) defines a longitudinal axis that is commonly referred to below as a shaft axis (SA). Except as otherwise described below, instrument (310) described below may be constructed and operable like instrument (10) described above. Certain details of instrument (310) will therefore be omitted from the following description, it being understood that such details are already provided above in the description of instrument (10).

Instrument (310) may have a modular configuration such that shaft (322) is selectively removable from, and selectively attachable to, handle portion (320). Instrument (310) is configured similarly to instrument (10), such that the operability and use of instrument (310) is the same as described above for instrument (10) with the added feature of instrument (310) having a modular configuration. With its modular configuration, instrument (310) provides a way to change the desired end effector. In addition to or in lieu of the foregoing, features operable for providing the modular configuration of instrument (310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

As discussed in greater detail below, end effector (312) is provided on shaft (322) and is operable to compress, staple, and cut tissue. End effector (312) may be used in place of end effector (12) shown in FIG. 1. In some versions, end effector (312) may be integrally formed with shaft (322) or, alternatively, may be separately formed and subsequently combined. In some versions, end effector (312) may be provided for use in robotic systems. In such robotic systems, modular shaft (322) having end effector (312) may be attachable to a portion of the robotic system for use such that handle portion (320) is replaced by components of the robotic system, including a body. Other ways to incorporate an end effector (312) having placement tip (314) into a user operated or robotic operated instrument will be apparent to those of ordinary skill in the art.

Figure 11:
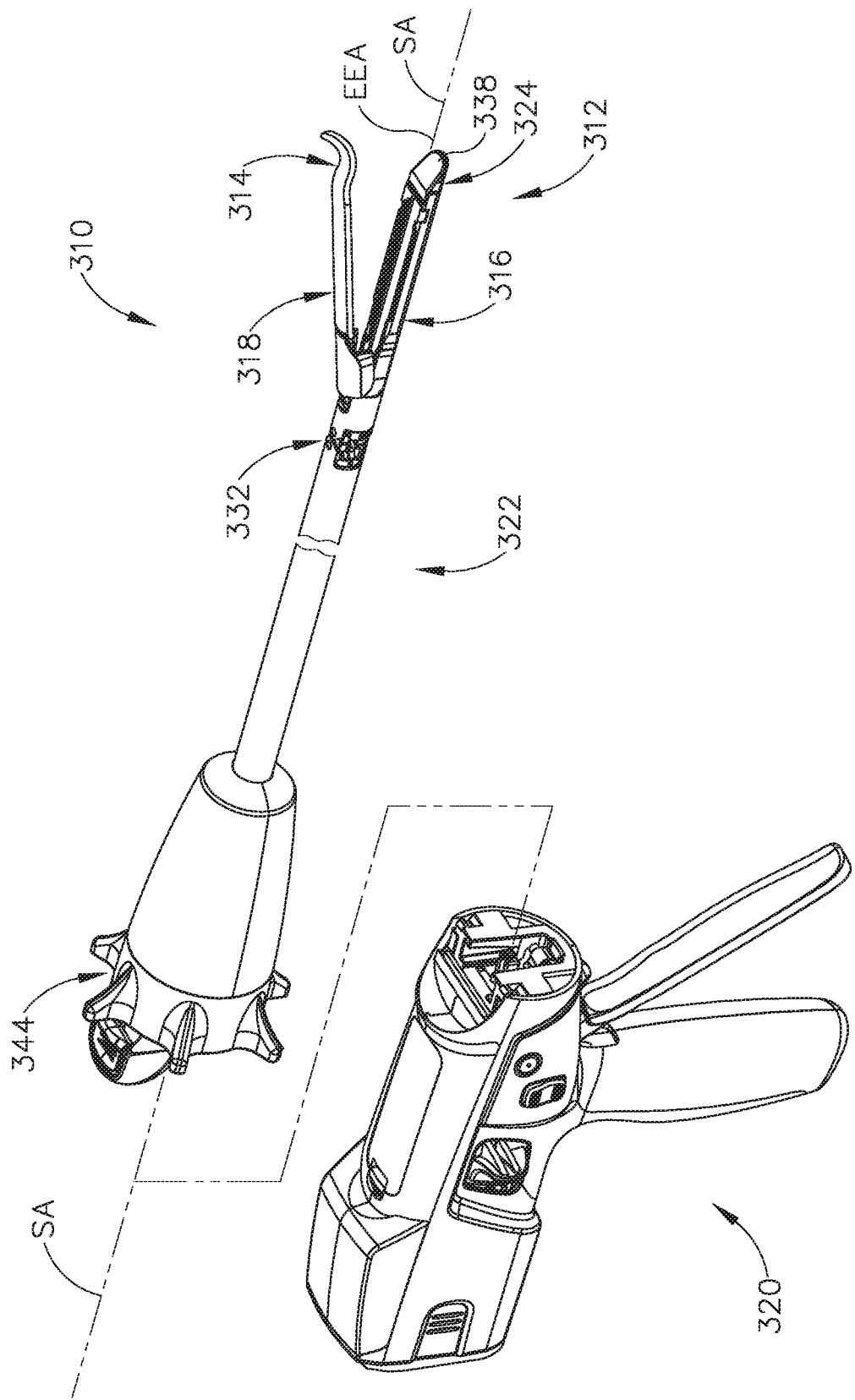
FIG. 11 depicts a perspective view of a second exemplary surgical stapling instrument including a third exemplary end effector and a first exemplary placement tip, where the upper and lower jaws are in an open configuration.

Placement tip (314) is operable to elastically deform from a non-deflected position to a deflected position. Placement tip (314) obtains the non-deflected position when end effector (312) is not clamping tissue. More specifically, in this non-deflected position, end effector (312) may be in the open configuration as shown in FIG. 11, or in the closed configuration as shown in FIGS. 8 and 9 with respect to end effector (212). In instances when end effector (312) is in this non-deflected position, end effector (312) may be considered in a non-loaded state or non-loaded position. Conversely, in the deflected position (not shown) when end effector (312) is clamping tissue, end effector (312) may be considered in a loaded state or a loaded position. In the deflected position, at least a portion of placement tip (314) deflects upwardly. The deflected position for placement tip (314) may be substantially straight in some versions, but may be deflected to a degree (e.g., slightly above or slightly below shaft axis (SA)) in other versions. It should be understood that the deflected position for placement tip (314) may be defined by the characteristics (e.g., thickness, density, etc.) of the tissue that is being captured between anvil (318) and lower jaw (316), thereby causing the deflection of placement tip (314). In some variations, placement tip (314) does not deflect in response to a load.

It should also be understood that the teachings herein may be readily combined with various teachings in U.S. Patent Pub. No. 2020/0015812, entitled "Surgical Stapling End Effector Component with Deformable Tip Skewing in Multiple Planes," published Jan. 16, 2020, the disclosure of which is incorporated by reference herein. Various suitable ways in which the teachings herein may be combined with the teachings of U.S. Patent Pub. No. 2020/0015812 will be apparent to those of ordinary skill in the art.

A. Second Exemplary Surgical Instrument Including Third End Effector with First Example of Placement Tip FIGS. 12A-12E show enlarged views of a distal end of end effector (312). Placement tip (314) is located adjacent at least one of distal end (321) of anvil (318) or a distal end of lower jaw (316). As shown in FIGS. 11 and 12A-12E, placement tip (314) is coupled with a distal end (321) of anvil (318). Placement tip (314) may be permanently secured to anvil (318), or alternatively, placement tip (314) may be removable coupled with anvil (318). Placement tip (314) may be integrally formed together with anvil (318) as unitary piece or consist of separately formed components. Placement tip (314) may be positioned on the same jaw as staple cartridge (324) or on the same jaw as anvil (318). As shown in FIGS. 11 and 12A-12E, upper jaw includes anvil (318), while lower jaw (316) is removably coupled with staple cartridge (324). However, this relationship may be reversed if desired. Staple cartridge (324) is configured to hold one or more staples in a manner similar to staple cartridge (37).

As previously described, at least one of anvil (318) or lower jaw (316) is movable relative to other of anvil (318) or lower jaw (316) between the open configuration and the closed configuration. As shown, anvil (318) pivotably rotates toward lower jaw (316) in the same manner as anvil (18) as described above with respect to instrument (10). In this manner, end effector (312) is like end effector (12), except for the laterally deflected configuration and deformability of placement tip (314). In the closed configuration, a portion of placement tip (314) may in abutting contact with an angled surface (338) of staple cartridge (324); or alternatively, a lateral gap may exist between placement tip (314) and staple cartridge (324). Additionally, as shown in the top view of FIGS. 12A-12E, lower jaw (316) is generally longer and wider than anvil (318) and placement tip (314). However, lower jaw (316) may be shorter and/or and narrower than anvil (318) and placement tip (314) if desired.

FIGS. 11 and 12A-12E show placement tip (314) as including a proximal portion (326), a central portion (328), and a distal portion (330). Proximal portion (326) extends distally from distal end (321) of anvil (318) and is disposed opposite from lower jaw (316). Central portion (328) is disposed longitudinally between proximal and distal portions (326, 330). Proximal portion (326), central portion (328) and distal portion (330) of placement tip (314) each include an asymmetric profile along the longitudinal axis of shaft (322), i.e. shaft axis (SA). As shown in the top views of FIGS. 12A-12E, proximal portion (326) tapers inwardly along an inwardly tapering portion (329) on the left side (when viewed from above), while the opposite right side extends arcuately toward distal portion (330).

Distal portion (330) includes a tip axis (TA) defined by the direction to which a tip (334) of distal portion (330) extends. Tip (334) includes a proximal surface (340) and a distal surface (342), with proximal surface (340) extending outwardly from inwardly tapering portion (329). In the example shown, tip axis (TA) is measured using proximal surface (340) of tip (334). Alternatively, other surfaces (e.g. distal surface (342) may also be used. Moreover, shaft axis (SA) and tip axis (TA) define an angle that is selectively adjustable. For improved clarity, a modified shaft axis (SA') is respectively shown in FIGS. 12A-12E to better visualize angle theta ($\theta1$-$\theta5$) generally formed between shaft axis (SA) and tip axis (TA). A modified shaft axis (SA') is offset from and extends parallel to shaft axis (SA). Additionally, as shown in FIGS. 12A-12E, tip axis (TA) is generally perpendicular to the longitudinal axis of end effector (312), which is referred herein as end effector axis (EEA).

As previously described with respect to instrument (10), instrument (310) is shown as including an articulation joint (332) that pivotably couples shaft (322) with end effector (312). Articulation joint (332) may be the same or similar to articulation joint (11) described above, with details pertaining to articulation joint (332) being omitted for the sake of brevity. Articulation joint (332) is configured to enable end effector (312) to pivot laterally relative to shaft (322). As shown in FIGS. 12A-12E, modified shaft axis (SA') and tip axis (TA) collectively define various angle thetas ($\theta1$-$\theta5$), with angle theta being selectively adjustable using articulation joint (332). Articulation joint (332) may be selectively adjustable by a user using powered articulation. Alternatively, articulation joint (332) may be manually powered using articulation control (344) shown in FIG. 11. Articulation joint (332) moves end effector axis (EEA) relative to shaft axis (SA), resulting in a different angle theta ($\theta1$-$\theta5$).

Figure 12C:
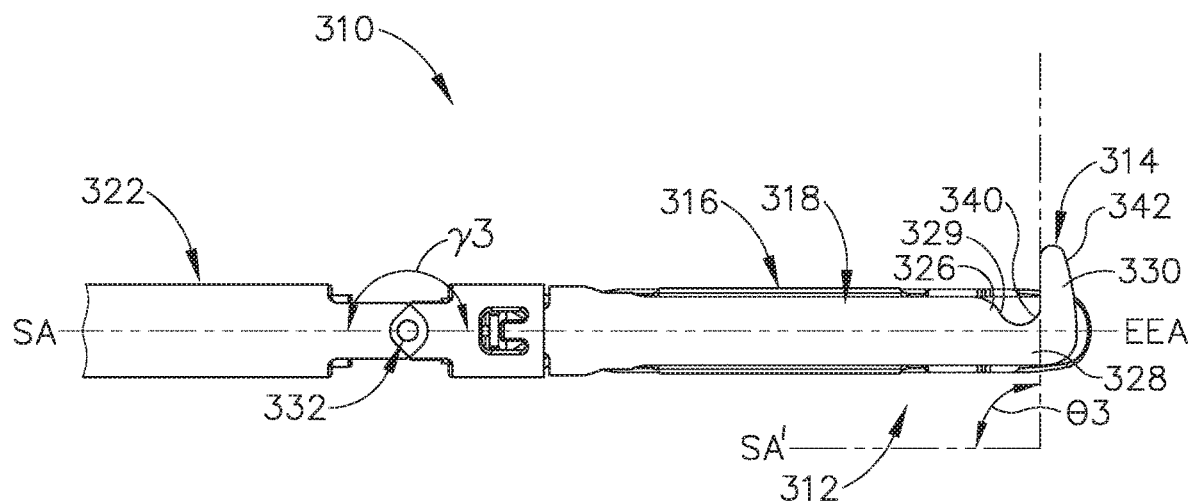
FIG. 12C depicts an enlarged top view of the end effector of FIG. 11 in a third angled position.

As described below in greater detail, FIGS. 12A-12E show various angle thetas ($\theta1$-$\theta5$) that are selectively adjustable between about 0 degrees to about 180 degrees. While FIGS. 12A-12E show angle theta ($\theta1$-$\theta5$) as five distinct angles, it is to be understood that angle theta may be any angle in between about 0 degrees to about 180 degrees as well. For example, FIG. 12A shows angle theta ($\theta1$) defined by modified shaft axis (SA') and tip axis (TA) being about 0 degrees, such that shaft axis (SA) and tip axis (TA) extend generally parallel to one another. End effector axis (EEA) extends approximately perpendicular to both shaft axis (SA1) and tip axis (TA), such that angle gamma ($\gamma1$) is 90 degrees. When angle theta ($\theta1$) is 0 degrees, tip (314) of distal portion (330) is directed parallel to the shaft axis (SA). Tip (314) is also oriented proximally relative to shaft (322) in the state shown in FIG. 12A.

FIG. 12B shows angle theta ($\theta2$) being about 45 degrees and measured between modified shaft axis (SA') and tip axis (TA). Angle gamma ($\gamma2$) is about 135 degrees and is measured between shaft axis (SA) and end effector axis (EEA).

FIG. 12C shows angle theta ($\theta3$) being about 90 degrees and measured between modified shaft axis (SA') and tip axis (TA). Additionally, angle gamma ($\gamma3$) is about 180 degrees measured between shaft axis (SA) and end effector axis (EEA).

Figure 12D:
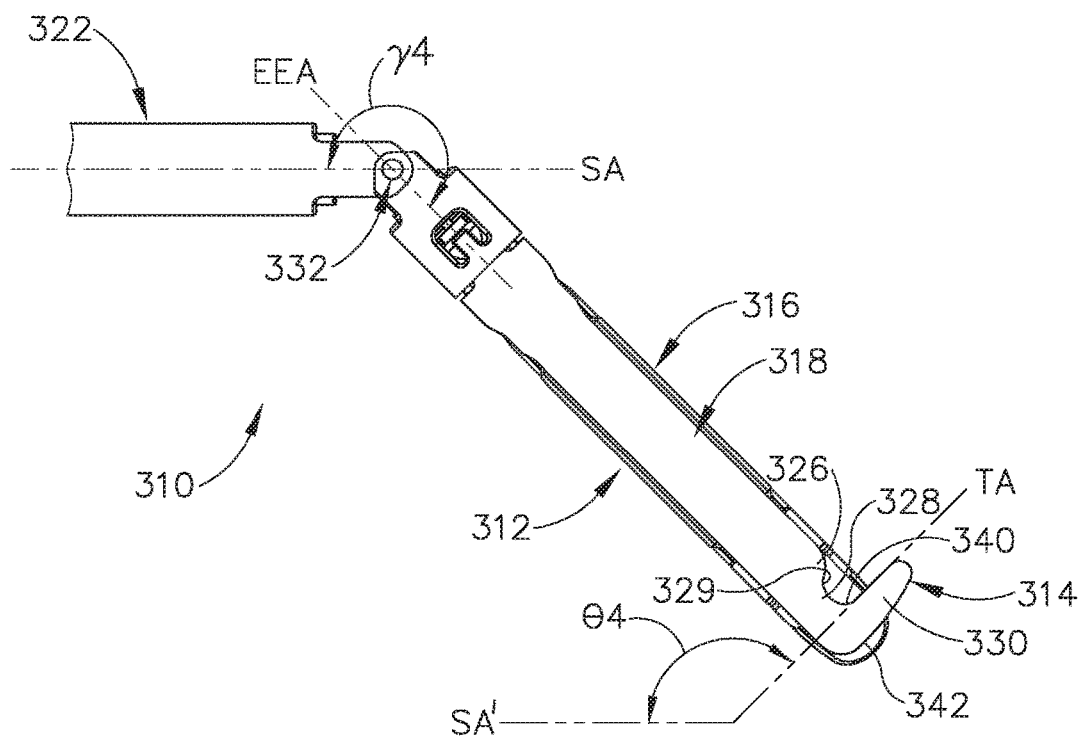
FIG. 12D depicts an enlarged top view of the end effector of FIG. 11 in a fourth angled position.

FIG. 12D shows angle theta ($\theta4$) being about 135 degrees and measured between modified shaft axis (SA') and tip axis (TA). Additionally, angle gamma ($\gamma4$) is about 225 degrees measured between shaft axis (SA) and end effector axis (EEA).

Figure 12E:
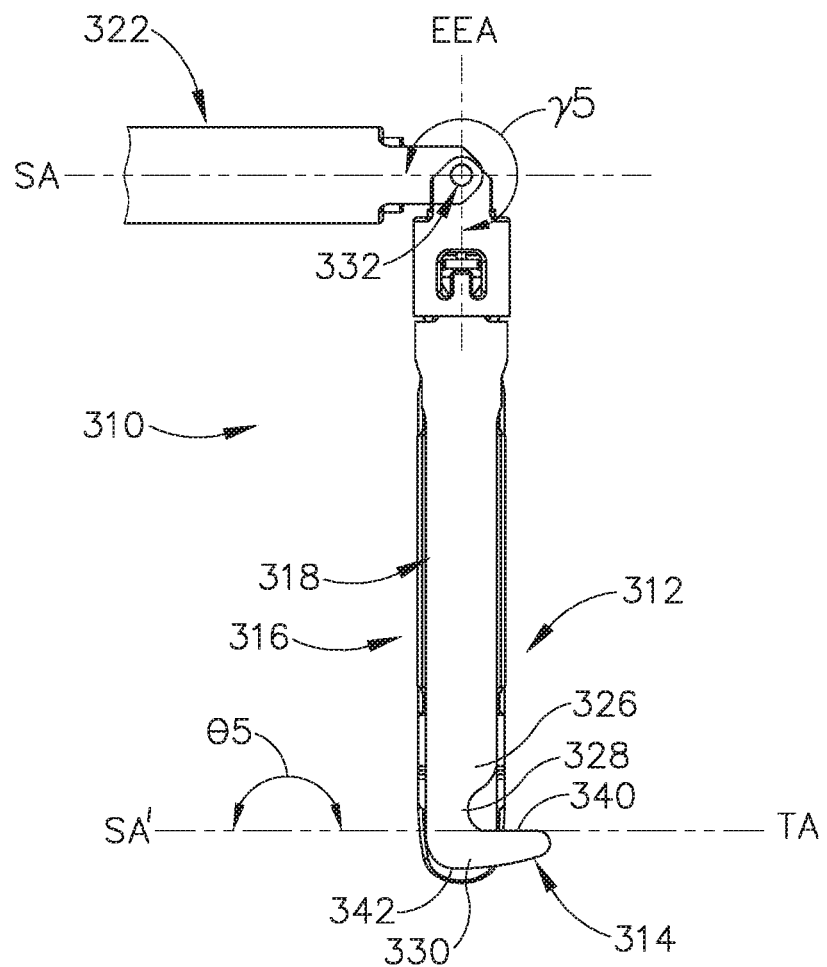
FIG. 12E depicts an enlarged top view of the end effector of FIG. 11 in a fifth angled position.

FIG. 12E shows angle theta ($\theta5$) being about 180 degrees and measured between modified shaft axis (SA') and tip axis (TA). Additionally, angle gamma ($\gamma5$) is about 270 degrees measured between shaft axis (SA) and end effector axis (EEA). When the angle theta ($\theta5$) is 180 degrees, tip (314) of distal portion (330) is directed parallel to shaft axis (SA). Tip (314) is also oriented distally relative to shaft (322) in the state shown in FIG. 12E.

Assuming the position of FIG. 12C of end effector (312) is a baseline position, like FIG. 11, when tip angle ($\theta3$) is 90 degrees, shaft axis (SA) is parallel to end effector axis (EEA). Moreover, assuming FIG. 12C is the baseline position, angle theta ($\theta1$-$\theta2$) as shown in FIGS. 12A and 12B, forms an acute angle along a first direction of articulation (shown as a counter clockwise rotation). Conversely, angle theta ($\theta4$-$\theta5$) as shown in FIGS. 12D and 12E forms an obtuse angle along a second direction of articulation, that is opposite the first direction of articulation (shown as a clockwise rotation).

B. Exemplary Method of Operating Instrument

Figure 13A:
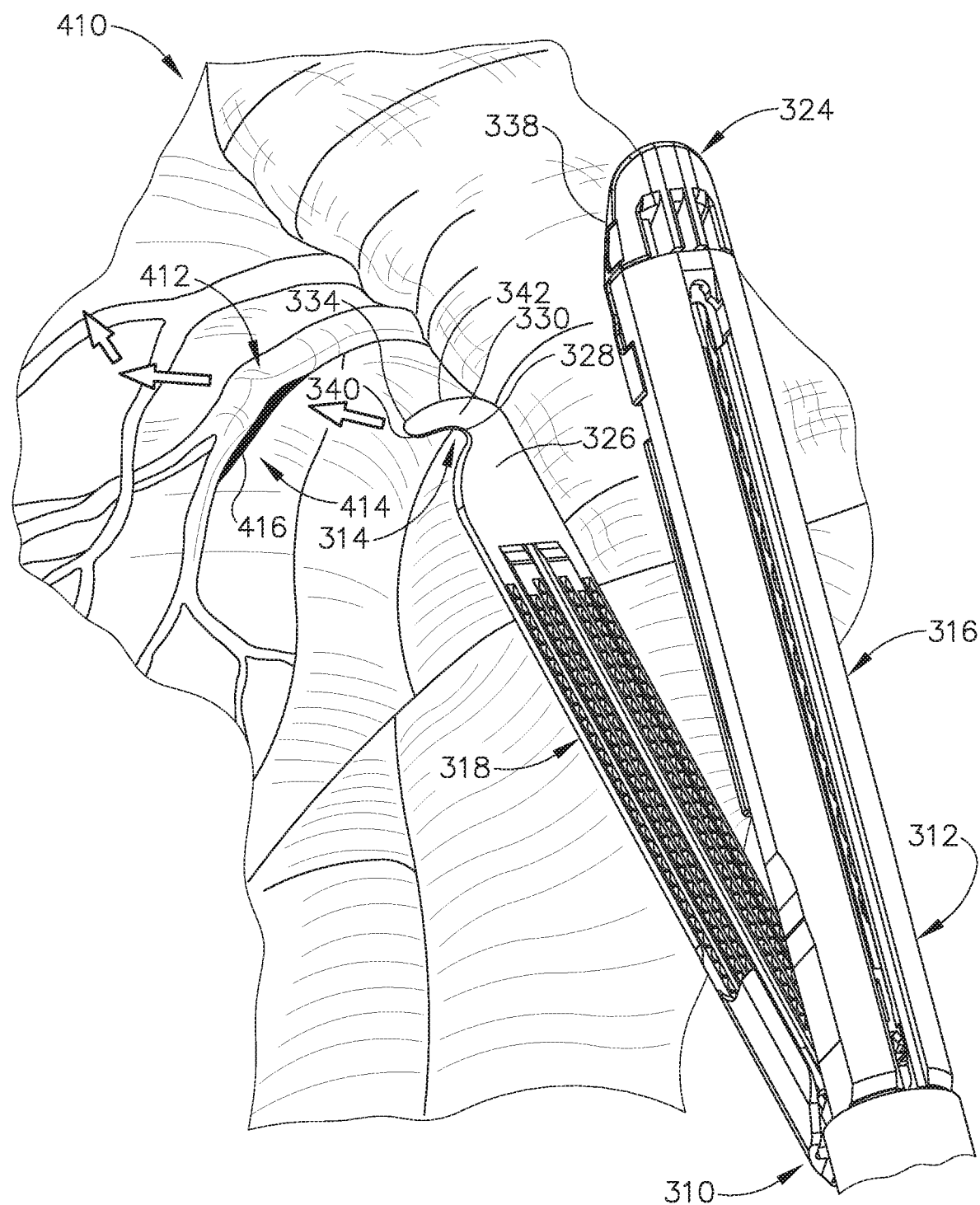
FIG. 13A depicts an enlarged perspective view of the end effector of FIG. 11 prior to entering a tissue opening.

FIGS. 13A-13D show an exemplary method of operating instrument (310) for contacting tissue (410). As shown, instrument (310) again includes end effector (312), placement tip (314), lower jaw (316), anvil (318), shaft (322), staple cartridge (324), proximal portion (326), central portion (328), distal portion (330), tip (334), angled surface (338), proximal surface (340), and distal surface (342). FIG. 13A shows instrument (310) being introduced toward already separated first and second layers (412, 414) of tissue (410). First and second layers (412, 414) collectively define a tissue opening (416). As shown, instrument (310) is in the open configuration. While not shown, it is also envisioned that upper jaw and lower jaw (316) may be in the closed configuration. Additionally, the shape of placement tip (314) may vary if desired.

Figure 13B:
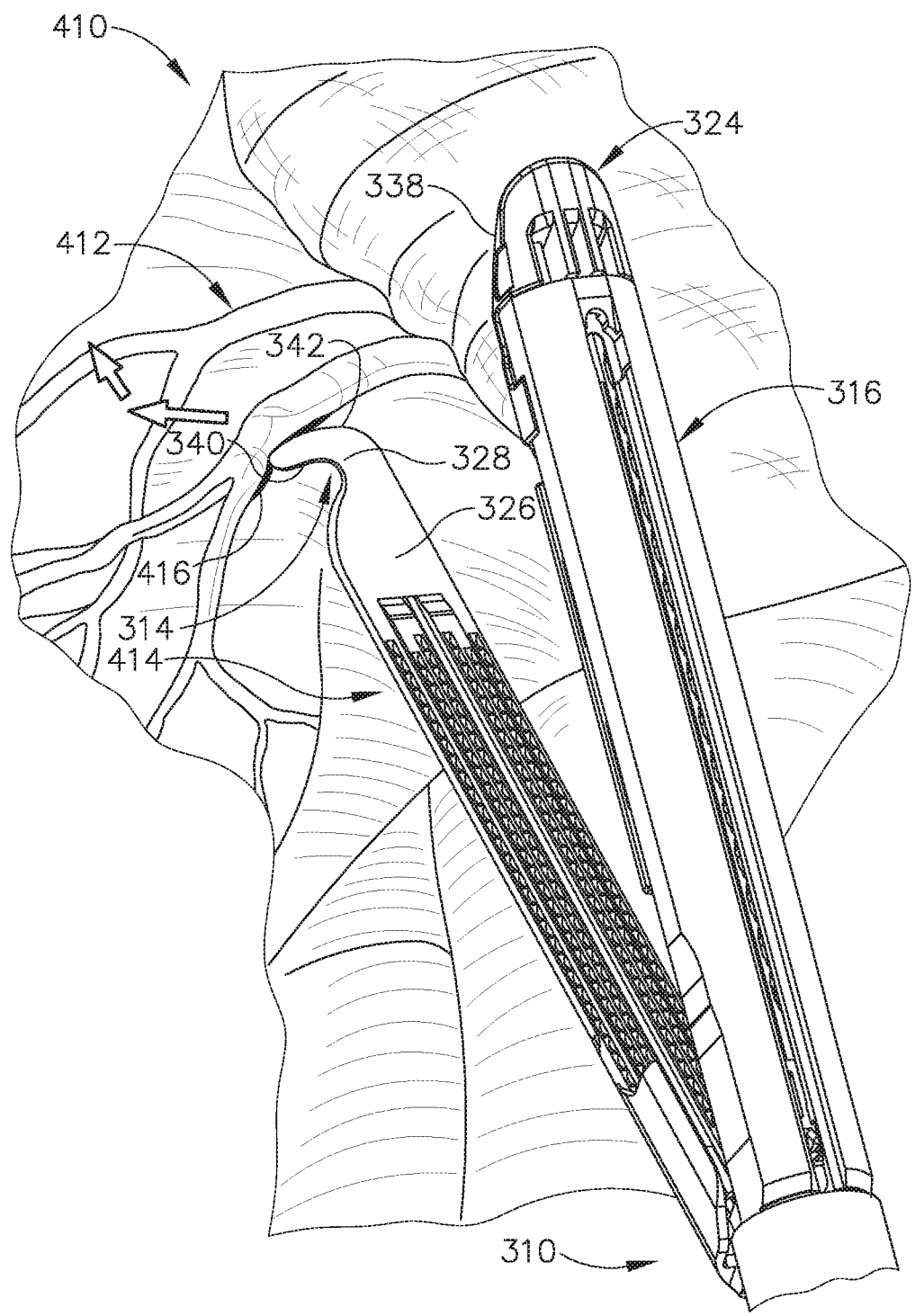
FIG. 13B depicts a perspective view of the end effector of FIG. 11 moving laterally to a second position entering the tissue opening of FIG. 13A.

FIG. 13B shows instrument (310) being moved laterally toward already separated first and second layers (412, 414) of tissue (410) that collectively define tissue opening (416). As shown, tip (334) of placement tip (314) enters an already formed tissue opening (416). Placement tip (314) does not perform dissection of tissue (410), which includes separation of first and second layers (412, 414) to form tissue opening (416). Instead, first and second layers (412, 414) of tissue (410) are already separated using any one of a variety of known methods and devices. In some other variations, placement tip (314) provides at least some blunt dissection of tissue (e.g., separating different anatomical structures apart from each other) as end effector (312) is moved in the patient.

Figure 13C:
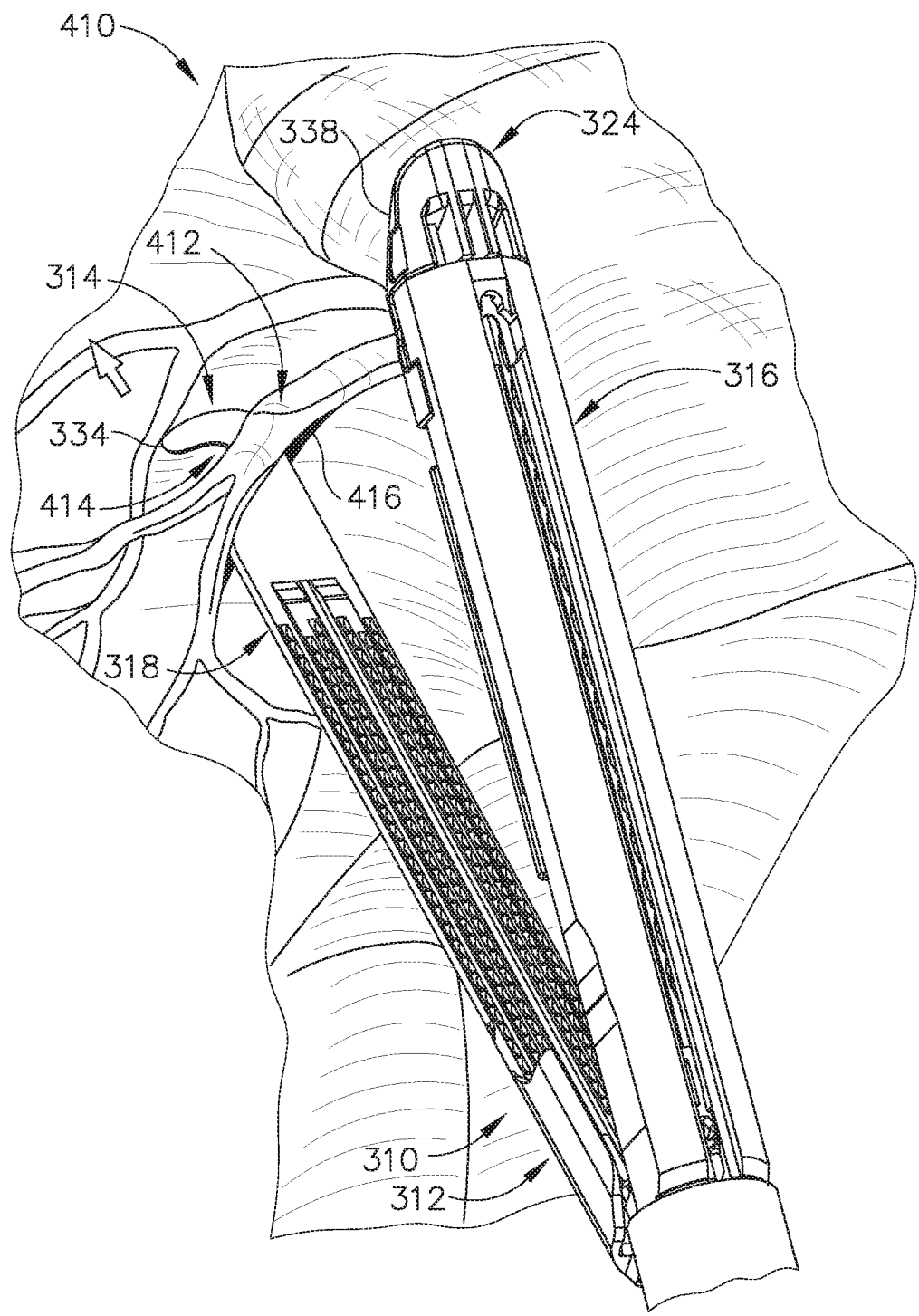
FIG. 13C depicts a perspective view of the end effector of FIG. 11 moving laterally to a third position already through the tissue opening of FIG. 13A.

FIG. 13C shows placement tip (314) of instrument (310) moving laterally through tissue opening (416). Placing placement tip (314) through tissue opening (416) may be obtained using only a lateral motion in this example. As previously indicated, central portion (328) and distal portion (330) have an asymmetric profile along tip axis (TA) of placement tip (314). As shown, distal portion (330) is now through already separated first and second layers of tissue (412, 414).

Figure 13D:
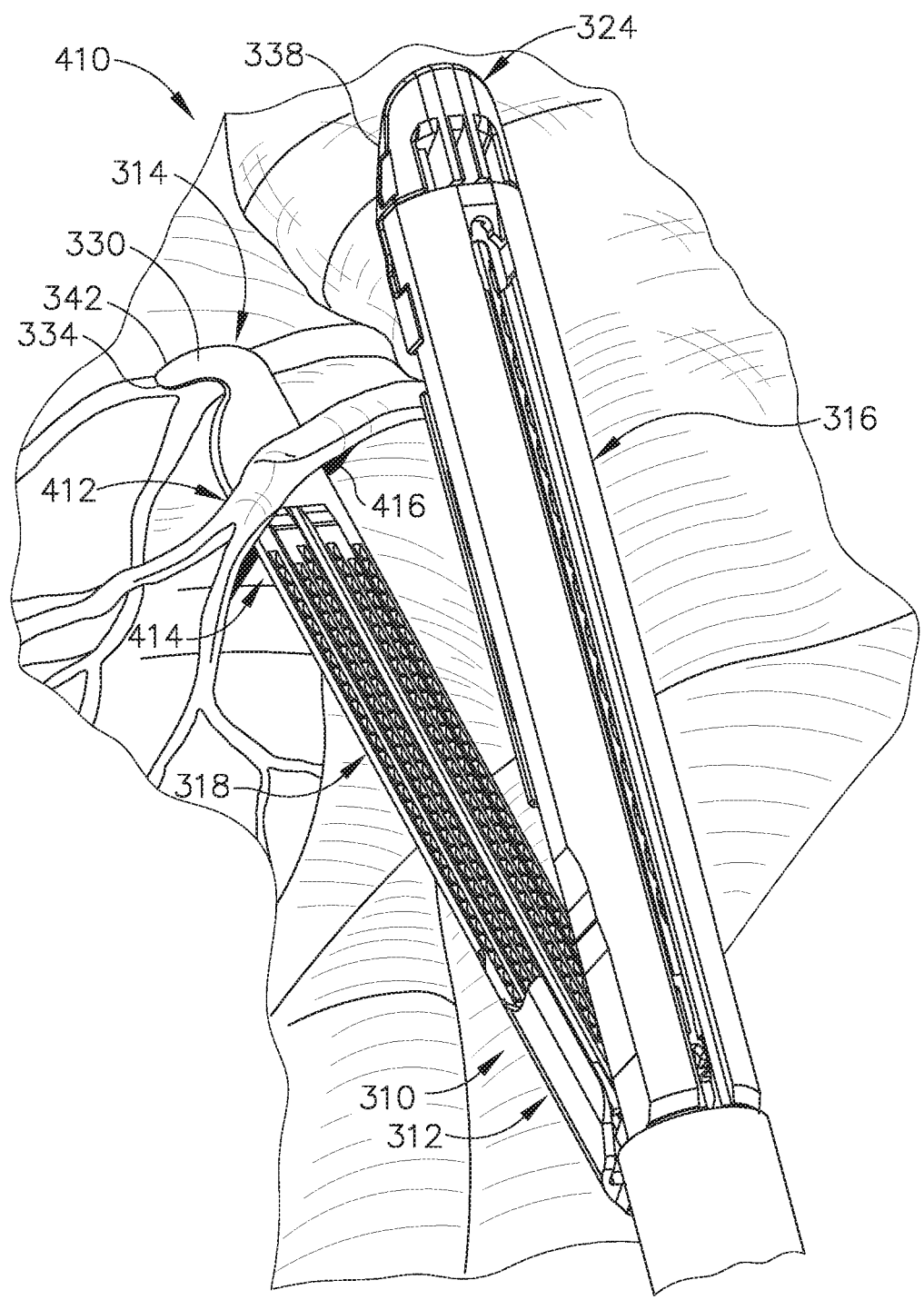
FIG. 13D depicts a perspective view of the end effector of FIG. 11 moved distally to a fourth position after moving laterally through the tissue opening of FIG. 13A.

FIG. 13D shows placement tip (314) subsequently advancing (314) distally once already through tissue opening (416). According to the perspective view of FIG. 13D, distally is shown as being upwards and to the left. This of course may vary given the position of tissue (410). After reaching the state shown in FIG. 13D, the operator may further position end effector (312) such that tissue (412) (e.g., a vessel targeted for transection) is positioned between staple forming pockets of anvil (318) and corresponding staple apertures of the staple cartridge. The operator may then actuate end effector (312) to transect and staple the tissue (412).

Instrument (310) according to this example may include articulation joint (332) to rotate end effector (312) to the desired angle, in a manner similar or different to that described above with respect to FIGS. 12A-12E. Laterally moving open jaw of instrument (310) through tissue opening (416) may include the user selectively adjusting articulation joint (332) manually or using powered articulation as described previously with respect to instrument (10, 310).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument, comprising: (a) a body; (b) a shaft extending from the body and defining a shaft axis extending longitudinally along the shaft; and (c) an end effector in communication with the shaft, wherein the end effector is operable to compress, staple, and cut tissue, wherein the end effector comprises: (i) first and second opposing jaws, wherein at least one of the first and second jaws is movable relative to the other of the first and second jaws between an open position and a closed position, (ii) a staple cartridge configured to hold one or more staples, wherein the staple cartridge is coupled with the second jaw, and (iii) a placement tip extending from a distal end of the first jaw or a distal end of the second jaw, wherein the placement tip includes proximal and distal portions, wherein the distal portion includes an asymmetric profile along the longitudinal axis of the shaft, and wherein the distal portion includes a tip axis defined by a tip of the distal portion, wherein the shaft axis and the tip axis define an angle that is selectively adjustable.

Example 2

The instrument of Example 1, further comprising an articulation joint coupling the shaft with the end effector, wherein the articulation joint is configured to enable the end effector to pivot relative to the shaft, wherein the shaft axis and the tip axis define an angle that is selectively adjustable using the articulation joint.

Example 3

The instrument of Example 2, wherein the articulation joint is selectively adjustable by a user.

Example 4

The instrument of any one or more of Examples 1 through 3, wherein the angle is selectively adjustable between about 0 degrees to about 180 degrees.

Example 5

The instrument of any one or more of Examples 1 through 4, wherein the angle is selectively adjustable between about 45 degrees to about 135 degrees.

Example 6

The instrument of any one or more of Examples 1 through 5, wherein the angle is selectively adjustable from an acute angle along a first direction of articulation to an obtuse angle along a second direction of articulation, wherein the second direction is opposite the first direction.

Example 7

The instrument of any one or more of Examples 1 through 6, wherein when the angle is 180 degrees, the tip of the distal portion is directed parallel to the shaft axis.

Example 8

The instrument of any one or more of Examples 1 through 7, wherein the tip axis extends perpendicular to an end effector axis that extends longitudinally along the end effector.

Example 9

The instrument of any one or more of Examples 1 through 8, wherein the first jaw includes an anvil and the placement tip, and the second jaw includes the staple cartridge.

Example 10

The instrument of Example 9, wherein the placement tip is permanently secured to the anvil.

Example 11

The instrument of any one or more of Examples 1 through 10, wherein the jaw disposed opposite the placement tip extends distally beyond the tip of the distal portion of the placement tip.

Example 12

The instrument of any one or more of Examples 1 through 11, wherein the tip of the distal portion extends laterally beyond the width of the jaw disposed opposite the placement tip.

Example 13

An instrument, comprising: (a) a body; (b) a shaft extending from the body and defining a shaft axis extending longitudinally along the shaft; and (c) an end effector in communication with the shaft, wherein the end effector is operable to compress, staple, and cut tissue, wherein the end effector comprises: (i) first and second opposing jaws, wherein at least one of the first and second jaws is movable relative to the other of the first and second jaws between an open position and a closed position, (ii) a staple cartridge configured to hold one or more staples, wherein the staple cartridge is coupled with the second jaw, and (iii) a placement tip extending laterally from a distal end of the first jaw or a distal end of the second jaw, wherein the placement tip includes proximal and distal portions, and wherein the distal portion includes a tip axis defined by a tip of the distal portion; and (d) an articulation joint coupling the shaft with the end effector, wherein the articulation joint is configured to enable the end effector to pivot relative to the shaft, wherein the shaft axis and the tip axis define an angle that is selectively adjustable using the articulation joint, wherein the angle is selectively adjustable between about 0 degrees to about 180 degrees.

Example 14

The instrument of Example 13, wherein the angle is selectively adjustable from an acute angle along a first direction of articulation to an obtuse angle along a second direction of articulation, wherein the second direction is opposite the first direction.

Example 15

The instrument of any one or more of Examples 13 through 14, wherein the distal portion has an asymmetric profile along the longitudinal axis of the shaft.

Example 16

A method of operating an instrument, the method comprising: (a) placing a placement tip of a jaw of the instrument between first and second layers of tissue that collectively define a tissue opening, wherein the placement tip is oriented along a tip axis that is laterally oriented in relation to a longitudinal axis of a proximal portion of the jaw; and (b) laterally moving the placement tip of the instrument along the tip axis through the tissue opening.

Example 17

The method of Example 16, wherein placing the placement tip further comprises placing the placement tip through the tissue opening using only a lateral motion.

Example 18

The method of any one or more of Examples 16 through 17, further comprising subsequently advancing the placement tip distally through the tissue opening.

Example 19

The method of any one or more of Examples 16 through 18, wherein the placement tip extends from a distal end of the jaw, wherein the placement tip includes proximal and distal portions, wherein the distal portion has an asymmetric profile along a longitudinal axis of the placement tip, and wherein placing the placement tip comprises placing the distal portion having the asymmetric profile between already separated first and second layers of tissue.

Example 20

The method of any one or more of Examples 16 through 19, wherein the instrument includes an articulation joint operatively coupled with the shaft, wherein laterally moving the open jaw of the instrument through the tissue opening comprises a user selectively adjusting the articulation joint.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. Patent Pub. No. 2018/0325516, entitled "Method of Surgical Stapling with End Effector Component Having a Curved Tip," published Nov. 15, 2018, the disclosure of which is incorporated by reference herein. Various suitable ways in which the teachings herein may be combined with the teachings of U.S. Patent Pub. No. 2018/0325516 will be apparent to those of ordinary skill in the art.

It should also be understood that the teachings herein may be readily combined with various teachings in U.S. Patent Pub. No. 2018/0325515, entitled "Surgical Stapling End Effector Jaw with Tip Deflecting Toward Other Jaw," published Nov. 15, 2018, the disclosure of which is incorporated by reference herein. Various suitable ways in which the teachings herein may be combined with the teachings of U.S. Patent Pub. No. 2018/0325515 will be apparent to those of ordinary skill in the art.

It should also be understood that the teachings herein may be readily combined with various teachings in U.S. Patent Pub. No. 2018/0325514, entitled "Surgical Stapling End Effector Component with Tip Having Varying Bend Angle," published Nov. 15, 2018, filed the disclosure of which is incorporated by reference herein. Various suitable ways in which the teachings herein may be combined with the teachings of U.S. Patent Pub. No. 2018/0325514 will be apparent to those of ordinary skill in the art.

It should also be understood that the teachings herein may be readily combined with various teachings in U.S. Patent Pub. No. 2020/0015815, entitled "Permanent Attachment Means for Curved Tip of Component of Surgical Stapling Instrument," published Jan. 16, 2020, issued as U.S. Pat. No. 10,973,515 on Apr. 13, 2021, the disclosure of which is incorporated by reference herein. Various suitable ways in which the teachings herein may be combined with the teachings of U.S. Patent Pub. No. 2020/0015815, issued as U.S. Pat. No. 10,973,515 on Apr. 13, 2021, will be apparent to those of ordinary skill in the art.

It should also be understood that the teachings herein may be readily combined with various teachings in U.S. Patent Pub. No. 2020/0015811, entitled "Surgical Stapling End Effector Component with Deformable Tip Having Void," published Jan. 16, 2020, issued as U.S. Pat. No. 10,789,252 on Sep. 29, 2020, filed on even date herewith, the disclosure of which is incorporated by reference herein. Various suitable ways in which the teachings herein may be combined with the teachings of U.S. Patent Pub. No. 2020/0015811, issued as U.S. Pat. No. 10,789,252 on Sep. 29, 2020, will be apparent to those of ordinary skill in the art.

It should also be understood that the teachings herein may be readily combined with various teachings in U.S. Patent Pub. No. 2020/0015814, entitled "Surgical Stapling End Effector Component with Deformable Tip Having Thick Distal End," published Jan. 16, 2020, issued as U.S. Pat. No. 10,912,558 on Feb. 9, 2021, filed on even date herewith, the disclosure of which is incorporated by reference herein. Various suitable ways in which the teachings herein may be combined with the teachings of U.S. Patent Pub. No. 2020/0015814, issued as U.S. Pat. No. 10,912,558 on Feb. 9, 2021, will be apparent to those of ordinary skill in the art.

It should also be understood that the teachings herein may be readily combined with various teachings in U.S. Patent Pub. No. 2020/0015817, entitled "Buttress Applier Cartridge for Surgical Stapler Having End Effector with Deflectable Curved Tip," published Jan. 16, 2020, issued as U.S. Pat. No. 10,912,561 on Feb. 9, 2021, the disclosure of which is incorporated by reference herein. Various suitable ways in which the teachings herein may be combined with the teachings of U.S. Patent Pub. No. 2020/0015817, issued as U.S. Pat. No. 10,912,561 on Feb. 9, 2021, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument, comprising:
(a) a body;
(b) a shaft extending from the body and defining a shaft axis extending longitudinally along the shaft; and
(c) an end effector in communication with the shaft, wherein the end effector defines an end effector axis extending longitudinally along the end effector, wherein the end effector is operable to compress, staple, and cut tissue, wherein the end effector comprises:
 (i) first and second opposing jaws, wherein at least one of the first and second jaws is movable relative to the other of the first and second jaws between an open position and a closed position,
 (ii) a stapling assembly configured to hold one or more staples, wherein the stapling assembly is coupled with the second jaw, wherein the stapling assembly has a maximum width, and
 (iii) a placement tip extending from a distal end of the first jaw or a distal end of the second jaw, wherein the placement tip includes proximal and distal portions, wherein the distal portion includes a non-mirrored profile about a plane that extends through the proximal portion of the placement tip and extends parallel to the end effector axis, wherein the proximal portion tapers inwardly relative to an outer periphery of the proximal portion and away from a tip of the distal portion, wherein the distal portion includes a tip axis that extends through the tip of the distal portion, wherein the tip of the distal portion has a maximum width taken perpendicular to the end effector axis that is greater than the maximum width of the stapling assembly such that the tip extends laterally beyond the stapling assembly, wherein the tip is rounded,
wherein the shaft axis and the tip axis define an angle that is selectively adjustable.

2. The instrument of claim 1, further comprising an articulation joint coupling the shaft with the end effector, wherein the articulation joint is configured to enable the end effector to pivot relative to the shaft, wherein the angle is selectively adjustable using the articulation joint.

3. The instrument of claim 1, wherein the angle is selectively adjustable about a single pivot point between about 0 degrees to about 180 degrees.

4. The instrument of claim 1, wherein the angle is selectively adjustable about a single pivot point between about 45 degrees to about 135 degrees.

5. The instrument of claim 1, wherein the angle is selectively adjustable from an acute angle along a first direction of articulation to an obtuse angle along a second direction of articulation, wherein the second direction is opposite the first direction.

6. The instrument of claim 3, wherein when the angle is 180 degrees, the tip of the distal portion is directed parallel to the shaft axis.

7. The instrument of claim 1, wherein the tip axis extends perpendicular to the end effector axis.

8. The instrument of claim 1, wherein the stapling assembly includes a staple cartridge, wherein the first jaw includes an anvil and the placement tip, and the second jaw includes the staple cartridge.

9. The instrument of claim 1, wherein the jaw disposed opposite the placement tip extends distally beyond the tip of the distal portion of the placement tip.

10. The instrument of claim 1, wherein the tip includes a proximal surface and a distal surface, wherein the distal surface tapers proximally in a direction toward an end of the tip, wherein the proximal surface does not taper proximally in the direction toward the end of the tip.

11. An instrument, comprising:
(a) a body;
(b) a shaft extending from the body and defining a shaft axis extending longitudinally along the shaft; and
(c) an end effector in communication with the shaft and defining an end effector axis extending longitudinally along the end effector, wherein the end effector is operable to compress, staple, and cut tissue, wherein the end effector comprises:
(i) first and second opposing jaws, wherein at least one of the first and second jaws is movable relative to the other of the first and second jaws between an open position and a closed position, and
(ii) a placement tip extending from a distal end of the first jaw or a distal end of the second jaw, wherein the placement tip includes proximal and distal portions, wherein the distal portion includes a non-mirrored profile about a plane that extends through the proximal portion of the placement tip and extends parallel to the end effector axis, wherein the distal portion includes a tip, wherein the tip includes a proximal surface and a distal surface, wherein the proximal surface of the distal portion extends along a tip axis, wherein the distal surface tapers proximally in a direction toward an end of the tip, wherein the proximal surface does not taper proximally in the direction toward the end of the tip,
wherein the shaft axis and the tip axis define an angle that is selectively adjustable about a single pivot point between about 0 degrees to about 180 degrees, wherein when the angle is 180 degrees the proximal surface of the tip is directed parallel to the shaft axis.

12. The instrument of claim 11, wherein the placement tip includes an inwardly tapering portion, wherein the proximal surface extends outwardly from the inwardly tapering portion toward the tip.

13. The instrument of claim 11, wherein the jaw disposed opposite the placement tip extends distally beyond the tip of the distal portion of the placement tip.

14. The instrument of claim 11, wherein the tip of the distal portion extends laterally beyond the width of the jaw disposed opposite the placement tip.

15. The instrument of claim 11, wherein the proximal portion tapers inwardly relative to an outer periphery of the proximal portion and away from the tip of the distal portion.

16. An instrument, comprising:
(a) a body;
(b) a shaft extending from the body and defining a shaft axis extending longitudinally along the shaft; and
(c) an end effector in communication with the shaft, wherein the end effector is operable to compress, staple, and cut tissue, wherein the end effector comprises:
(i) first and second opposing jaws, wherein at least one of the first and second jaws is movable relative to the other of the first and second jaws between an open position and a closed position, and
(ii) a placement tip extending from a distal end of the first jaw or a distal end of the second jaw, wherein the placement tip includes proximal and distal portions, wherein the distal portion includes an asymmetric profile, wherein the distal portion includes a tip axis extending through a tip of the distal portion, wherein the tip of the distal portion extends laterally beyond the width of the jaw disposed opposite the placement tip, wherein the proximal portion includes an inwardly tapering portion that tapers inwardly relative to an outer periphery of the proximal portion and away from the tip of the distal portion,
wherein the shaft axis and the tip axis define an angle that is selectively adjustable.

17. The instrument of claim 16, wherein the jaw disposed opposite the placement tip extends distally beyond the tip of the distal portion of the placement tip.

18. The instrument of claim 16, wherein the angle defined by the shaft axis and the tip axis is selectively adjustable about a single pivot point between about 0 degrees to about 180 degrees, wherein when the angle is 180 degrees the proximal surface of the tip is directed parallel to the shaft axis.

* * * * *